US012576034B2

(12) United States Patent
Bhat et al.

(10) Patent No.: US 12,576,034 B2
(45) Date of Patent: Mar. 17, 2026

(54) FORMULATIONS OF (+)-2-[1-(3-ETHOXY-4-METHOXY-PHENYL)-2-METHANESULFONYL-ETHYL]-4-ACETYLAMINOISOINDOLINE-1,3-DIONE

(71) Applicant: AMGEN INC., Thousand Oaks, CA (US)

(72) Inventors: Sreenivas S. Bhat, Kendall Park, NJ (US); Michael T. Kelly, Lake Hopatcong, NJ (US)

(73) Assignee: AMGEN INC., Thousand Oaks, CA (US)

( * ) Notice: Subject to any disclaimer, the term of this patent is extended or adjusted under 35 U.S.C. 154(b) by 339 days.

(21) Appl. No.: 16/874,424

(22) Filed: May 14, 2020

(65) Prior Publication Data

US 2021/0093573 A1 Apr. 1, 2021

Related U.S. Application Data

(63) Continuation of application No. 13/727,366, filed on Dec. 26, 2012, now abandoned.

(60) Provisional application No. 61/580,626, filed on Dec. 27, 2011.

(51) Int. Cl.

| | |
|---|---|
| ***A61K 31/4035*** | (2006.01) |
| ***A61K 9/20*** | (2006.01) |
| ***A61K 9/28*** | (2006.01) |

(52) U.S. Cl.

CPC .......... *A61K 9/2013* (2013.01); *A61K 9/2018* (2013.01); *A61K 9/2054* (2013.01); *A61K 9/2813* (2013.01); *A61K 9/2826* (2013.01); *A61K 9/284* (2013.01); *A61K 9/2853* (2013.01); *A61K 9/2866* (2013.01); *A61K 31/4035* (2013.01)

(58) Field of Classification Search

CPC .. A61K 9/2013; A61K 9/2054; A61K 9/2813; A61K 9/2826; A61K 9/284; A61K 9/2853; A61K 9/2866; A61K 31/4035; A61K 9/2018; A61P 17/06; A61P 19/06; A61P 29/00; A61P 1/04; A61P 17/00; A61P 19/02; A61P 27/02

See application file for complete search history.

(56) References Cited

U.S. PATENT DOCUMENTS

| | | | | |
|---|---|---|---|---|
| 5,358,941 A ‡ | 10/1994 | Bechard | A61K 9/2018 | 514/102 |
| 5,632,984 A ‡ | 5/1997 | Wong | A61K 9/0048 | 424/42 |
| 5,635,517 A ‡ | 6/1997 | Muller | A61K 9/107 | 514/32 |
| 5,641,513 A | 6/1997 | Lech et al. | | |
| 5,770,589 A ‡ | 6/1998 | Billson | A61K 31/58 | 514/17 |
| 5,800,819 A ‡ | 9/1998 | Wambebe | A61P 7/00 | 424/73 |
| 6,001,368 A ‡ | 12/1999 | Jenks | A23L 33/11 | 62/646 |
| 6,015,803 A ‡ | 1/2000 | Wirostko | A61K 31/395 | 514/15 |
| 6,020,358 A ‡ | 2/2000 | Muller | A61P 31/00 | 514/411 |
| 6,218,369 B1 ‡ | 4/2001 | Bombardelli | A61K 36/28 | 514/34 |
| 6,225,348 B1 ‡ | 5/2001 | Paulsen | A61K 9/0048 | 514/53 |
| 6,281,230 B1 ‡ | 8/2001 | Muller | A61P 19/00 | 514/32 |
| 6,448,323 B1 ‡ | 9/2002 | Jordan | C08K 3/34 | 524/145 |
| 6,962,940 B2 ‡ | 11/2005 | Muller | A61P 35/00 | 514/41 |
| 7,208,516 B2 | 4/2007 | Muller et al. | | |
| 7,276,529 B2 | 10/2007 | Muller et al. | | |
| 7,427,638 B2 | 9/2008 | Muller et al. | | |
| 7,659,302 B2 | 2/2010 | Muller et al. | | |
| 2002/0054899 A1 ‡ | 5/2002 | Zeldis | A61P 9/10 | 424/42 |
| 2003/0212112 A1 * | 11/2003 | Murdoch | A61K 9/2027 | 514/340 |
| 2004/0029832 A1 ‡ | 2/2004 | Zeldis | A61P 27/02 | 514/58 |

(Continued)

FOREIGN PATENT DOCUMENTS

| | | | |
|---|---|---|---|
| EP | 2196465 A1 * | 6/2010 | C07D 401/04 |
| WO | WO-98/03502 A1 ‡ | 1/1998 | A61K 9/0019 |

(Continued)

OTHER PUBLICATIONS

Jivraj, M. et al., An Overview of the Different Excipients Useful for the Direct Compression of Tablets, Feb. 2000, PSTT, vol. 3, No. 2, 6 pages. (Year: 2000).*

Pages, L. et al., PDE4 Inhibitors: A Review of Current Develops (2005-2009), 2009, Expert Opinion on Therapeutic Patents, vol. 19, No. 11, pp. 1501-1519. (Year: 2009).*

Dick et al. (International Journal of Pharmaceutics, 38 (1987) 23-31. (Year: 1987).*

(Continued)

*Primary Examiner* — Mina Haghighatian
*Assistant Examiner* — Susannah S Armstrong
(74) *Attorney, Agent, or Firm* — MARSHALL, GERSTEIN & BORUN LLP

(57) ABSTRACT

Pharmaceutical compositions and single unit dosage forms of (+)-2-[1-(3-ethoxy-4-methoxy-phenyl)-2-methanesulfonyl-ethyl]-4-acetylaminoisoindoline-1,3-dione, or a pharmaceutically acceptable stereoisomer, prodrug, salt, solvate, hydrate, or clathrate thereof, are provided herein. Also provided are methods of treating, managing, or preventing various diseases or disorders.

21 Claims, No Drawings

(56) References Cited

U.S. PATENT DOCUMENTS

| | | | | |
|---|---|---|---|---|
| 2004/0087546 | A1 ‡ | 5/2004 | Zeldis | A61K 31/454 514/58 |
| 2004/0091455 | A1 ‡ | 5/2004 | Zeldis | A61K 38/27 424/85 |
| 2004/0190609 | A1 ‡ | 9/2004 | Watanabe | H04N 19/15 375/24 |
| 2004/0220144 | A1 ‡ | 11/2004 | Zeldis | A61P 7/06 514/58 |
| 2005/0100529 | A1 ‡ | 5/2005 | Zeldis | A61K 38/193 424/85 |
| 2005/0143344 | A1 ‡ | 6/2005 | Zeldis | A61P 21/00 514/58 |
| 2005/0143420 | A1 ‡ | 6/2005 | Moutouh-de Parseval | A61K 38/19 514/32 |
| 2005/0203142 | A1 ‡ | 9/2005 | Zeldis | A61P 43/00 514/32 |
| 2005/0214328 | A1 ‡ | 9/2005 | Zeldis | A61K 36/28 424/23 |
| 2005/0222209 | A1 ‡ | 10/2005 | Zeldis | A61P 25/24 514/32 |
| 2005/0239842 | A1 ‡ | 10/2005 | Zeldis | A61P 33/12 514/32 |
| 2006/0030594 | A1 ‡ | 2/2006 | Zeldis | A61K 31/198 514/32 |
| 2006/0122228 | A1 ‡ | 6/2006 | Zeldis | A61P 25/08 514/32 |
| 2006/0154880 | A1 ‡ | 7/2006 | Hensel | A61K 31/65 514/28 |
| 2006/0183766 | A1 ‡ | 8/2006 | Boni | A61P 3/10 514/291 |
| 2006/0188475 | A1 ‡ | 8/2006 | Xu | A61K 31/454 424/85 |
| 2006/0257471 | A1 * | 11/2006 | Ettema | C07D 215/227 424/464 |
| 2006/0269600 | A1 * | 11/2006 | Dietrich | A61P 11/06 424/464 |
| 2007/0048327 | A1 ‡ | 3/2007 | Bartlett | A61P 37/04 424/18 |
| 2007/0155791 | A1 ‡ | 7/2007 | Zeldis et al. | A61P 17/00 514/32 |
| 2008/0234359 | A1 | 9/2008 | Muller et al. | |
| 2011/0065691 | A1 * | 3/2011 | Kaplan | C07D 401/14 435/375 |
| 2011/0207826 | A1 * | 8/2011 | Schwarz | A61K 47/38 514/263.34 |

FOREIGN PATENT DOCUMENTS

| | | | | |
|---|---|---|---|---|
| WO | WO-1998/03502 | A1 | 1/1998 | |
| WO | WO-98/54170 | A1 ‡ | 3/1998 | A61K 9/4866 |
| WO | WO-1998/54170 | A1 | 12/1998 | |
| WO | WO-2001/04195 | A1 | 1/2001 | |
| WO | WO-03/080049 | A1 ‡ | 10/2003 | A61P 9/00 |
| WO | WO-2003/080048 | A1 | 10/2003 | |
| WO | WO-2003/080049 | A1 | 10/2003 | |
| WO | WO-2004/103274 | A2 ‡ | 12/2004 | A61P 1/02 |
| WO | WO-2006/111980 | A2 | 10/2006 | |
| WO | WO-2007/079182 | A1 ‡ | 7/2007 | A61K 31/454 |
| WO | WO-2009/120167 | A1 | 10/2009 | |
| WO | WO-2010/093588 | A1 ‡ | 8/2010 | A61K 45/06 |
| WO | WO-2011/060290 | A2 ‡ | 5/2011 | A61P 27/12 |
| WO | WO-2011063102 | A1 | 5/2011 | |
| WO | WO-2012/083017 | A2 | 6/2012 | |
| WO | WO-2013/101810 | A1 ‡ | 7/2013 | A61K 9/2826 |

OTHER PUBLICATIONS

Food and Drug Administration (FDA). (2003). Guidance for Industry Q1A(R2) Stability Testing of New Drug Substances and Product (Year: 2003).*

Rassu et al. (2006). Tableting properties of an improved spray-dried lactose, Journal of Drug Delivery Science and Technology, 16(6), p. 455-459, (Year: 2006).*

Carstensen, Drug Stability: Principles & Practices, Second Edition, Marcel Dekker, New York, NY, pp. 379-380 (1995).‡

Symptom ad causes—Osteoarthritis (published online by Mayo Clinic) (Year: 2019).‡

Symptom ad causes—Psoriasis (published online by Mayo Clinic) (Year: 2019).‡

Symptom ad causes—Crohn's disease (published online by Mayo Clinic) (Year: 2019).‡

Symptom ad causes—sarcoidosis (published online by Mayo Clinic) (Year: 2019).‡

Porter et al.; "Development, Optimization, and Scale-up of Process Parameters: Pan Coating;" Developing Solid Oral Dosage Forms: Pharmaceutical Theory and Practice; 2009; pp. 761-805.

Bharate et al., Interactions and incompatibilities of pharmaceutical excipients with active pharmaceutical ingredients: a comprehensive review, J. Excipients and Food Chemicals, pp. 3-26 (Dec. 2010).

"Symptoms and causes—Crohn's disease" (published online by Mayo Clinic) (Year: 2019).

"Symptoms and causes—Osteoarthritis" (published online by Mayo Clinic) (Year: 2019).

"Symptoms and causes—Psoriasis" (published online by Mayo Clinic) (Year: 2019).

"Symptoms and causes—sarcoidosis" (published online by Mayo Clinic) (Year: 2019).

Papp et al., "Efficacy of apremilast in the treatment of moderate to severe psoriasis: a randomised controlled trial," *Lancet*, 380:738-746 (2012).

Schafer, "Apremilast mechanism of action and application to psoriasis and psoriatic arthritis," *Biochem. Pharmacol.*, 83(12); 1583-1590 (2012).

Schett et al., "Oral apremilast in the treatment of active psoriatic arthritis: results of a multicenter, randomized, double-blind, placebo-controlled study," *Arthritis Rheum.*, 64(10):3156-3167 (2012).

Wu et al, "First-time-in-man, safety/tolerability and pharmacokinetics of ascending oral doses of apremilast (APR) in healthy subjects (HS)," *J. Invest Ann.*, 131:S86 abstract 515 (2011).

Hayashi et al., A Data-Driven Approach to Predicting Tablet Properties after Accelerated Test Using Raw Material Property Databse and Machine Learning, Chem. Pharm. Bull. 71(6):406-415(2023).

Gohel et al., "A review of co-processed directly compressible excipients", Journal of Pharmacy and Pharmaceutical Sciences, 8(1):76-93 (Apr. 2005).

Vromans et al., "Studies on tableting properties of lactose: Part 2. Consolidation and compaction of different types of crystalline lactose", Pharmaceutisch Weekblad, 7(5):186-193 (Oct. 1985).

* cited by examiner
‡ imported from a related application

FORMULATIONS OF (+)-2-[1-(3-ETHOXY-4-METHOXY-PHENYL)-2-METHANESULFONYL-ETHYL]-4-ACETYLAMINOISOINDOLINE-1,3-DIONE

CROSS REFERENCE TO RELATED APPLICATIONS

This application claims the benefit of priority to U.S. Provisional Patent Application Ser. No. 61/580,626, filed Dec. 27, 2011, the disclosure of which is incorporated by reference herein in its entirety.

1. FIELD

Provided herein are formulations and dosage forms of (+)-2-[1-(3-ethoxy-4-methoxy-phenyl)-2-methanesulfonyl-ethyl]-4-acetylaminoisoindoline-1,3-dione. Methods of using the formulations and dosage forms are also provided herein.

2. BACKGROUND

Drug substances are usually administered as part of a formulation in combination with one or more other agents that serve varied and specialized pharmaceutical functions. Dosage forms of various types may be made through selective use of pharmaceutical excipients. As pharmaceutical excipients have various functions and contribute to the pharmaceutical formulations in many different ways, e.g., solubilization, dilution, thickening, stabilization, preservation, coloring, flavoring, etc. The properties that are commonly considered when formulating an active drug substance include bioavailability, ease of manufacture, ease of administration, and stability of the dosage form. Due to the varying properties of the active drug substance to be formulated, dosage forms typically require pharmaceutical excipients that are uniquely tailored to the active drug substance in order to achieve advantageous physical and pharmaceutical properties.

(+)-2-[1-(3-ethoxy-4-methoxy-phenyl)-2-methanesulfonyl-ethyl]-4-acetylaminoisoindoline-1,3-dione ("Compound A") is a compound with anti-inflammatory activity in clinical development for the treatment of a variety of chronic inflammatory conditions. Pharmacologically, Compound A blocks the degradation of cyclic adenosine monophosphate (cAMP) via inhibition of the phosphodiesterase type IV (PDE4) enzyme, resulting in an increase in cAMP in PDE4-expressing cells including monocytes, T cells, and neutrophils. Enzyme assay data using purified PDE4 enzyme from U937 human monocytic cells indicate that Compound A has a PDE4 $IC_{50}$ of about 74 nM. Compound A and methods for its synthesis are described, e.g., in U.S. Pat. No. 6,962,940, the disclosure of which is hereby incorporated by reference in its entirety.

Due to its diversified pharmacological properties, Compound A is useful in treating, preventing, and/or managing various diseases or disorders. Thus, a need exists as to dosage forms of Compound A having advantageous physical and pharmaceutical properties.

3. SUMMARY

Provided herein are pharmaceutical dosage forms of (+)-2-[1-(3-ethoxy-4-methoxy-phenyl)-2-methanesulfonyl-ethyl]-4-acetylaminoisoindoline-1,3-dione ("Compound A"), or a pharmaceutically acceptable prodrug, salt, solvate, hydrate, or clathrate thereof. Also provided herein are methods of treating, managing, or preventing diseases and conditions such as, but not limited to, cancer, pain, Macular Degeneration, a skin disease, a pulmonary disorder, an asbestos-related disorder, a parasitic disease, an immunodeficiency disorder, a CNS disorder, CNS injury, atherosclerosis, a sleep disorder, hemoglobinopathy, anemia, an inflammatory disease, an autoimmune disease, a viral disease, a genetic disease, an allergic disease, a bacterial disease, an ocular neovascular disease, a choroidal neovascular disease, a retina neovascular disease, and rubeosis, using Compound A, or a pharmaceutically acceptable stereoisomer, prodrug, salt, solvate, hydrate, or clathrate thereof, in the dosage forms described herein.

4. DETAILED DESCRIPTION

4.1 Definitions

As used herein, the term "Compound A" refers to enantiomerically pure 2-[1-(3-ethoxy-4-methoxy-phenyl)-2-methanesulfonyl-ethyl]-4-acetylaminoisoindoline-1,3-dione. Without being limited by theory, Compound A is believed to be (+)-2-[1-(3-ethoxy-4-methoxy-phenyl)-2-methanesulfonyl-ethyl]-4-acetylaminoisoindoline-1,3-dione, which has the following structure:

Compound A

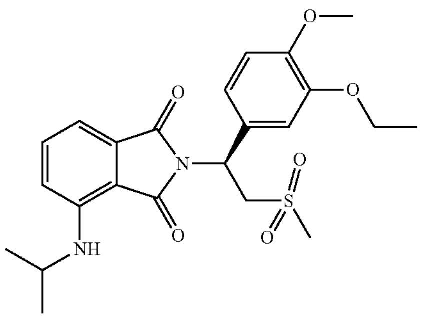

As used herein and unless otherwise indicated, a composition that is "substantially free" of a compound means that the composition contains less than about 20 percent by weight, more preferably less than about 10 percent by weight, even more preferably less than about 5 percent by weight, and most preferably less than about 3 percent by weight of the compound.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80 percent by weight of one stereoisomer of the compound and less than about 20 percent by weight of other stereoisomers of the compound, more preferably greater than about 90 percent by weight of one stereoisomer of the compound and less than about 10 percent by weight of the other stereoisomers of the compound, even more preferably greater than about 95 percent by weight of one stereoisomer of the compound and less than about 5 percent by weight of the other stereoisomers of the compound, and most preferably greater than about 97 percent by weight of one stereoisomer of the compound and less than about 3 percent by weight of the other stereoisomers of the compound.

As used herein and unless otherwise indicated, the term "enantiomerically pure" means a stereomerically pure composition of a compound having one chiral center.

As used herein, unless otherwise specified, the term "pharmaceutically acceptable salt(s)" includes, but is not limited to, salts of acidic or basic moieties of a compound provided herein. Basic moieties are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions. Suitable organic acids include, but are not limited to, maleic, fumaric, benzoic, ascorbic, succinic, acetic, formic, oxalic, propionic, tartaric, salicylic, citric, gluconic, lactic, mandelic, cinnamic, oleic, tannic, aspartic, stearic, palmitic, glycolic, glutamic, gluconic, glucaronic, saccharic, isonicotinic, methanesulfonic, ethanesulfonic, p-toluenesulfonic, benzenesulfonic acids, or pamoic (i.e., 1,1'-methylene-bis-(2-hydroxy-3-naphthoate) acids. Suitable inorganic acids include, but are not limited to, hydrochloric, hydrobromic, hydroiodic, sulfuric, phosphoric, or nitric acids. Compounds that include an amine moiety can form pharmaceutically acceptable salts with various amino acids, in addition to the acids mentioned above. Chemical moieties that are acidic in nature are capable of forming base salts with various pharmacologically acceptable cations. Examples of such salts are alkali metal or alkaline earth metal salts and, particularly, calcium, magnesium, sodium, lithium, zinc, potassium, or iron salts.

As used herein, and unless otherwise specified, the term "solvate" means a compound provided herein or a salt thereof, that further includes a stoichiometric or non-stoichiometric amount of solvent bound by non-covalent intermolecular forces. Where the solvent is water, the solvate is a hydrate.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of thalidomide that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of thalidomide that include —NO, —$NO_2$, —ONO, or —$ONO_2$ moieties.

As used herein and unless otherwise indicated, the terms "biohydrolyzable carbamate," "biohydrolyzable carbonate," "biohydrolyzable ureide," "biohydrolyzable phosphate" mean a carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein and unless otherwise indicated, the term "biohydrolyzable ester" means an ester of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein and unless otherwise indicated, the term "biohydrolyzable amide" means an amide of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable amides include, but are not limited to, lower alkyl amides, α-amino acid amides, alkoxyacyl amides, and alkylaminoalkylcarbonyl amides.

As used herein, and unless otherwise specified, the terms "treat," "treating" and "treatment" contemplate an action that occurs while a patient is suffering from the specified disease or disorder, which reduces the severity of the disease or disorder, or retards or slows the progression of the disease or disorder.

As used herein, and unless otherwise specified, the terms "prevent," "preventing" and "prevention" refer to the prevention of the onset, recurrence or spread of a disease or disorder, or of one or more symptoms thereof. The terms "prevent," "preventing" and "prevention" contemplate an action that occurs before a patient begins to suffer from the specified disease or disorder, which inhibits or reduces the severity of the disease or disorder.

As used herein, and unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

As used herein, and unless otherwise specified, the term "about," when used in connection with doses, amounts, or weight percent of ingredients of a composition or a dosage form, means dose, amount, or weight percent that is recognized by those of ordinary skill in the art to provide a pharmacological effect equivalent to that obtained from the specified dose, amount, or weight percent is encompassed. Specifically, the term "about" contemplates a dose, amount, or weight percent within 30%, 25%, 20%, 15%, 10%, 5%, 1%, 0.5%, or 0.25% of the specified dose, amount, or weight percent is encompassed.

As used herein, and unless otherwise specified, the term "stable," when used in connection with a formulation or a dosage form, means that the active ingredient of the formulation or dosage form remains solubilized for a specified amount of time and does not significantly degrade or aggregate or become otherwise modified (e.g., as determined, for example, by physical methods such as visual inspection or analytical methods such as HPLC).

4.2 Formulations and Dosage Forms

Provided herein are pharmaceutical formulations and dosage forms of (+)-2-[1-(3-ethoxy-4-methoxy-phenyl)-2- methanesulfonyl-ethyl]-4-acetylaminoisoindoline-1,3-dione (Compound A), or a pharmaceutically acceptable prodrug, salt, solvate, hydrate, or clathrate thereof. In some embodiments, the dosage forms are suitable for oral administration to a patient. In other embodiments, the formulations and dosage forms provided herein exhibit advantageous physical and/or pharmacological properties. Such properties include, but are not limited to, fast disintegration, low friability, ease of assay, content uniformity, flow properties for manufacture, dissolution and bioavailability, and/or stability. Also provided herein are kits comprising pharmaceutical formulations and dosage forms provided herein. Also provided herein are methods of treating, managing, and/or preventing a disease or condition, which comprises administering to a patient in need thereof a pharmaceutical formulation or a dosage form provided herein.

In some embodiments, the formulations and dosage forms provided herein are suitable for oral administration, in particular, in the form of a tablet. In certain embodiments, the formulations and dosage forms comprise a core containing the active ingredient and non-functional film coating.

In one embodiment, provided herein is a core formulation comprising Compound A. In one embodiment, the core formulation comprises Compound A in an amount of about 0.5% to about 30%, about 1% to about 25%, about 5% to about 25%, about 5% to about 20%, about 10% to about 15%, or about 5% to 15% by the weight of the total core composition. In one embodiment, the core formulation comprises Compound A in an amount of about 1%, 5%, 10%, 15%, 20% or 25% by the weight of the total core composition. In a specific embodiment, the core formulation comprises Compound A in an amount of about 10% by the weight of the total core composition.

In one embodiment, the core formulation comprising Compound A further comprises one or more fillers, disintegrants and/or lubricants.

In one embodiment, the filler is lactose. In a specific embodiment, the filler is lactose monohydrate (e.g., Fast-Flo®). In one embodiment, the core formulation comprises lactose in an amount of about 20% to about 85%, about 30% to about 75%, about 40% to about 70%, or about 50% to about 65% by weight of the total core composition. In one embodiment, the core formulation comprises lactose in an amount of about 20%, 30%, 40%, 50%, 60%, 70%, 80% or 85% by weight of the total core composition. In a specific embodiment, the core formulation comprises lactose in an amount of about 60% by weight of the total core composition.

In one embodiment, the filler is cellulose. In a specific embodiment, the filler is microcrystalline cellulose (e.g., Avicel®). In one embodiment, the core formulation comprises cellulose in an amount of about 5% to about 60%, about 10% to about 50%, about 15% to about 40%, about 20% to about 30%, or about 25% to about 30% by weight of the total core composition. In one embodiment, the core formulation comprises cellulose in an amount of about 5%, 10%, 15%, 20%, 25%, 30%, 35%, 40%, 45% and 50% by weight of the total core composition. In a specific embodiment, the core formulation comprises cellulose in an amount of about 26.25% by weight of the total core composition.

In one embodiment, formulations or dosage forms provided herein may contain two or more fillers.

In one embodiment, the disintegrant is croscarmellose. In a specific embodiment, the disintegrant is croscarmellose sodium (e.g., Ac-di-sol®). In one embodiment, the core formulation comprises croscarmellose in an amount of about 0.1% to about 10%, about 0.5% to about 8%, about 1% to about 5%, or about 2% to about 8% by weight of the total core composition. In one embodiment, the core formulation comprises croscarmellose in an amount of about 0.1%, 1%, 2%, 3%, 4%, 5%, 6%, 7% or 8% by weight of the total core composition. In a specific embodiment, the core formulation comprises croscarmellose in an amount of about 3% by weight of the total core composition.

In one embodiment, the lubricant is magnesium stearate. In one embodiment, the core formulation comprises magnesium stearate in an amount of about 0.1% to about 5%, about 0.25% to about 5%, about 0.3% to about 2%, about 0.5% to about 1%, or about 0.5% to about 2% by weight of the total core composition. In one embodiment, the core formulation comprises magnesium stearate in an amount of about 0.1%, 0.2%, 0.3%, 0.4%, 0.5%, 0.6%, 0.7%, 0.8%, 0.9% 1%, 2%, 3%, 4% or 5% by weight of the total core composition. In a specific embodiment, the core formulation comprises magnesium stearate in an amount of about % by weight of the total core composition.

In one embodiment, provided herein is a core formulation comprising: Compound A at an amount of about 10% by weight of the total core composition; lactose at an amount of about 60% by weight of the total core composition; microcrystalline cellulose at an amount of about 26.25% by weight of the total core composition; croscarmellose at an amount of about 3% by weight of the total core composition; and magnesium stearate at an amount of about 0.75% by weight of the total core composition.

Without being limited by a particular theory, color change (e.g., fading) is frequently observed in tablet formulations. This phenomenon, known as blooming effect, is caused when lower molecular weight material used in the formulation diffuses to the surface under higher temperature and humidity conditions. For example, excipients such as medium chain triglycerides, which are commonly used as plasticizers in film coatings can migrate or diffuse to the tablet surface causing the color change. However, the phenomenon is not always observed when lower molecular weight materials are used in formulations, i.e., presence of lower molecular weight materials may or may not cause blooming effect. It was discovered that interaction of a particular lower molecular weight material with other ingredients of the formulation, as well as the actual amount of the lower molecular weight material and other ingredients, are critical in assessing whether a particular formulation would exhibit instability in terms of change of color or appearance.

Accordingly, in certain embodiments, the formulations or dosage forms provided herein do not comprise a lower molecular weight excipient that may diffuse to the surface of the composition. In other embodiments, the oral formulations or dosage forms provided herein comprise a lower molecular weight excipient, but at an amount that does not trigger blooming effect. In other embodiments, the oral formulations or dosage forms provided herein comprise a lower molecular weight excipient in the presence of other excipients in a way that blooming effect is not observed in connection with the resulting formulations or dosage forms. Consequently, formulations and dosage forms provided herein exhibit improved stability, particularly in terms of change of color or appearance.

In one embodiment, provided herein are formulations for coating of tablets. In one embodiment, such formulations do not comprise medium chain triglycerides. In such an embodiment, the formulations may contain other various excipients such as, but not limited to, coating agents, binders, lubricants, stabilizing agents, plasticizers, adhesives, glidants, and/or diluents. In some embodiments, the coating formulations provided herein optionally contain coloring agents. These excipients are well-known in the art.

In one embodiment, provided herein are coating formulations that do not comprise medium chain triglycerides.

In one embodiment wherein coating formulations do not contain medium chain triglycerides, the excipient is polydextrose. In a specific embodiment, polydesctrose is polydextrose FCC. In one embodiment, polydexrose is present at an amount of about 10% to about 60%, about 15% to about 50%, about 20% to about 40%, or about 25% to about 30% by weight of the total coating formulation. In another embodiment, polydextrose is present at an amount of about 5%, 10%, 15%, 20%, 25% or 30% by weight of the total coating formulation. In a specific embodiment, polydextrose is present at an amount of about 26% by weight of the total coating formulation.

In one aspect of this embodiment, the excipient is hypromellose. In a specific embodiment, the excipient is hypromellose 15 cP. In one embodiment, hypromellose is present at an amount of about 10% to about 60%, about 15% to about 50%, about 25% to about 40%, or about 30% to about 35% by weight of the total coating formulation. In another embodiment, hypromellose is present at an amount of about 5%, 10%, 15%, 20%, 25%, 30% or 35% by weight of the total coating formulation. In a specific embodiment, hypromellose is present at an amount of about 31% by weight of the total coating formulation.

In another aspect of this embodiment, the excipient is talc. In one embodiment, talc is present at an amount of about 0.1% to about 25%, about 1% to about 20%, about 3% to about 15%, or about 5% to about 10% by weight of the total coating formulation. In another embodiment, talc is present at an amount of about 1%, 2%, 3%, 4%, 4%, 5%, 6%, 7%, 8%, 9% or 10% by weight of the total coating formulation. In a specific embodiment, talc is present at an amount of about 7% by weight of the total coating formulation.

In another aspect of this embodiment, the excipient is maltodextrin. In one embodiment, maltodextrin is present at an amount of about 0.1% to about 25%, about 1% to about 20%, about 3% to about 15%, or about 5% to about 10% by weight of the total coating formulation. In another embodiment, maltodextrin is present at an amount of about 1%, 2%, 3%, 4%, 4%, 5%, 6%, 7%, 8%, 9% or 10% by weight of the total coating formulation. In a specific embodiment, maltodextrin is present at an amount of about 5% by weight of the total coating formulation.

In another aspect of this embodiment, the excipients are one or more coloring agents, which can be useful in distinguishing dosage forms containing different amounts of active ingredient. Examples of coloring agents include, but are not limited to, iron oxides (e.g., red, yellow and black) and titanium dioxide. Appropriate coloring agents may be mixed to obtain a desired color of the coating formulation. In some embodiments, two or more coloring agents can be used in coating formulations. In one embodiment, the coloring agents comprise titanium dioxide and red iron oxide. In another embodiment, the coloring agents comprise titanium dioxide, red iron oxide, and yellow iron oxide. In another embodiment, the coloring agents comprise titanium dioxide, red iron oxide, yellow iron oxide, and black iron oxide.

In another aspect of this embodiment, the coloring agents are present at an amount of about 10% to about 60%, about 15% to about 50%, about 20% to about 40%, or about 25% to about 35% by weight of the total coating formulation. In another embodiment, the coloring agents are present at an amount of about 5%, 10%, 15%, 20%, 25%, 30% or 35% by weight of the total coating formulation. In a specific embodiment, the coloring agents are present at an amount of about 31% by weight of the total coating formulation.

In a specific embodiment, provided herein is a coating formulation comprising: polydextrose at an amount of about 26% by weight of the total coating formulation; hypromellose at an amount of about 31% by weight of the total coating formulation; talc at an amount of about 7% by weight of the total coating formulation; maltodextrin at an amount of about 5% by weight of the total coating formulation; and a mixture of coloring agents at an amount of about 31% by weight of the total coating formulation.

In another embodiment wherein coating formulations do not contain medium chain triglycerides, the excipient is polydextrose. In a specific embodiment, polydesctrose is polydextrose FCC. In one embodiment, polydexrose is present at an amount of about 10% to about 60%, about 15% to about 50%, about 20% to about 40%, or about 25% to about 30% by weight of the total coating formulation. In another embodiment, polydextrose is present at an amount of about 5%, 10%, 15%, 20%, 25% or 30% by weight of the total coating formulation. In a specific embodiment, polydextrose is present at an amount of about 26% by weight of the total coating formulation.

In one aspect of this embodiment, the excipient is hypromellose. In a specific embodiment, the excipient is hypromellose 15 cP. In one embodiment, hypromellose is present at an amount of about 10% to about 60%, about 15% to about 50%, about 25% to about 40%, or about 30% to about 35% by weight of the total coating formulation. In another embodiment, hypromellose is present at an amount of about 5%, 10%, 15%, 20%, 25%, 30% or 35% by weight of the total coating formulation. In a specific embodiment, hypromellose is present at an amount of about 31% by weight of the total coating formulation.

In another aspect of this embodiment, the excipient is talc. In one embodiment, talc is present at an amount of about 0.1% to about 25%, about 1% to about 20%, about 3% to about 15%, or about 5% to about 10% by weight of the total coating formulation. In another embodiment, talc is present at an amount of about 1%, 2%, 3%, 4%, 4%, 5%, 6%, 7%, 8%, 9% or 10% by weight of the total coating formulation. In a specific embodiment, talc is present at an amount of about 7% by weight of the total coating formulation.

In another aspect of this embodiment, the excipient is maltodextrin. In one embodiment, maltodextrin is present at an amount of about 0.1% to about 25%, about 1% to about 20%, about 3% to about 15%, or about 5% to about 10% by weight of the total coating formulation. In another embodiment, maltodextrin is present at an amount of about 1%, 2%, 3%, 4%, 4%, 5%, 6%, 7%, 8%, 9% or 10% by weight of the total coating formulation. In a specific embodiment, maltodextrin is present at an amount of about 5% by weight of the total coating formulation.

In another aspect of this embodiment, the excipient is triacetin. In one embodiment, triacetin is present at an amount of about 0.1% to about 20%, about 0.5% to about 25%, about 1% to about 10%, or about 1% to about 5% by weight of the total coating formulation. In another embodiment, triacetin is present at an amount of about 1%, 2%, 3%, 4%, 4%, 5%, 6%, 7%, 8%, 9% or 10% by weight of the total coating formulation. In a specific embodiment, triacetin is present at an amount of about 4% by weight of the total coating formulation.

In another aspect of this embodiment, the coloring agents are present at an amount of about 10% to about 60%, about 15% to about 50%, about 20% to about 40%, or about 25% to about 30% by weight of the total coating formulation. In another embodiment, the coloring agents are present at an amount of about 5%, 10%, 15%, 20%, 25% or 30% by weight of the total coating formulation. In a specific embodiment, the coloring agents are present at an amount of about 27% by weight of the total coating formulation.

In a specific embodiment, provided herein is a coating formulation comprising: polydextrose at an amount of about 26% by weight of the total coating formulation; hypromellose at an amount of about 31% by weight of the total coating formulation; talc at an amount of about 7% by weight of the total coating formulation; maltodextrin at an amount of about 5% by weight of the total coating formulation; triacetin at an amount of about 4% by weight of the total coating formulation; and a mixture of coloring agents at an amount of about 27% by weight of the total coating formulation.

In another embodiment wherein coating formulations do not contain medium chain triglycerides, the excipient is polyvinyl alcohol. In one embodiment, polyvinyl alcohol is present at an amount of about 20% to about 75%, about 25% to about 65%, about 30% to about 55%, or about 35% to about 45% by weight of the total coating formulation. In another embodiment, polyvinyl alcohol is present at an amount of about 10%, 20%, 30%, 40%, 50% or 60% by weight of the total coating formulation. In a specific embodiment, polyvinyl alcohol is present at an amount of about 40% by weight of the total coating formulation.

In one aspect of this embodiment, the excipient is polyethylene glycol. In one specific embodiment, the excipient is polyethylene glycol 3350. In one embodiment, polyethylene glycol is present at an amount of about 5% to about 50%, about 10% to about 40%, about 15% to about 30%, or about 20% to about 25% b y weight of the total coating formulation. In another embodiment, polyethylene glycol is present at an amount of about 10%, 20%, 30%, 40% or 50% by weight of the total coating formulation. In a specific embodiment, polyethylene glycol is present at an amount of about 20% (e.g., 20.2%) by weight of the total coating formulation.

In another aspect of this embodiment, the excipient is talc. In one embodiment, talc is present at an amount of about 1% to about 30%, about 3% to about 25%, about 5% to about 20%, or about 10% to about 15% by weight of the total coating formulation. In another embodiment, talc is present at an amount of about 1%, 5%, 10%, 15%, 20%, 25% or 30% by weight of the total coating formulation. In a specific embodiment, talc is present at an amount of about 15% (e.g., 14.8%) by weight of the total coating formulation.

In another aspect of this embodiment, the excipients are one or more coloring agents. In one embodiment, the coloring agents are present at an amount of about 10% to about 60%, about 15% to about 50%, about 20% to about 40%, or about 25% to about 30% by weight of the total coating formulation. In another embodiment, the coloring agents are present at an amount of about 5%, 10%, 15%, 20%, 25% or 30% by weight of the total coating formulation. In a specific embodiment, the coloring agents are present at an amount of about 25% by weight of the total coating formulation.

In a specific embodiment, provided herein is a coating formulation comprising: polyvinyl alcohol at an amount of about 40% by weight of the total coating formulation; polyethylene glycol at an amount of about 20% by weight of the total coating formulation; talc at an amount of about 15% by weight of the total coating formulation; and a mixture of coloring agents at an amount of about 25% by weight of the total coating formulation.

In another embodiment wherein coating formulations do not contain medium chain triglycerides, the excipient is lactose. In one embodiment, lactose is present at an amount of about 10% to about 60%, about 20% to about 50%, about 25% to about 40%, or about 30% to about 35% by weight of the total coating formulation. In another embodiment, lactose is present at an amount of about 5%, 15%, 25%, 35%, 45%, 55% or 65% by weight of the total coating formulation. In a specific embodiment, polyvinyl alcohol is present at an amount of about 33% by weight of the total coating formulation.

In one aspect of this embodiment, the excipient is hypromellose. In a specific embodiment, the excipient is hypromellose 6 cP. In one embodiment, hypromellose is present at an amount of about 10% to about 60%, about 15% to about 50%, about 25% to about 40%, or about 30% to about 35% by weight of the total coating formulation. In another embodiment, hypromellose is present at an amount of about 5%, 10%, 15%, 20%, 25%, 30% or 35% by weight of the total coating formulation. In a specific embodiment, hypromellose is present at an amount of about 31% by weight of the total coating formulation.

In another aspect of this embodiment, the excipient is polyethylene glycol. In one specific embodiment, the excipient is polyethylene glycol 3350. In one embodiment, polyethylene glycol is present at an amount of about 0.1% to about 20%, about 0.3% to about 10%, about 0.5% to about 15%, or about 1% to about 5% by weight of the total coating formulation. In another embodiment, polyethylene glycol is present at an amount of about 1%, 2%, 3%, 4%, 5%, 6%, 7%, 8%, 9% or 10% by weight of the total coating formulation. In a specific embodiment, polyethylene glycol is present at an amount of about 5% by weight of the total coating formulation.

In another aspect of this embodiment, the excipient is triacetin. In one embodiment, triacetin is present at an amount of about 0.1% to about 20%, about 0.5% to about 25%, about 1% to about 10%, or about 1% to about 5% by weight of the total coating formulation. In another embodiment, triacetin is present at an amount of about 1%, 2%, 3%, 4%, 5%, 6%, 7%, 8%, 9% or 10% by weight of the total coating formulation. In a specific embodiment, triacetin is present at an amount of about 4% by weight of the total coating formulation.

In another aspect of this embodiment, the excipients are one or more coloring agents. In one embodiment, the coloring agents are present at an amount of about 10% to about 60%, about 15% to about 50%, about 20% to about 40%, or about 25% to about 30% by weight of the total coating formulation. In another embodiment, the coloring agents are present at an amount of about 5%, 10%, 15%, 20%, 25% or 30% by weight of the total coating formulation. In a specific embodiment, the coloring agents are present at an amount of about 27% by weight of the total coating formulation.

In a specific embodiment, provided herein is a coating formulation comprising: lactose at an amount of about 33% by weight of the total coating formulation; hypromellose at an amount of about 31% by weight of the total coating formulation; polyethylene glycol at an amount of about 5% by weight of the total coating formulation; triacetin at an amount of about 4% by weight of the total coating formulation; and a mixture of coloring agents at an amount of about 27% of the total weight of the coating formulation.

In other embodiments, provided herein are coating formulations that contain medium chain triglycerides and other excipients, yet do not cause blooming effect, e.g., changes in color or appearance under storage.

In one embodiment where coating formulations contain medium chain triglycerides, medium chain triglycerides are present at an amount of about 0.1 to about 15%, about 0.5 to about 10%, about 1% to about 5%, or about 1% to 3% by weight of the total coating formulation. In another embodiment, medium chain triglycerides are present at an amount of about 0.1%, 0.5%, 1%, 1.5%, 2%, 2.5%, 3%, 3.5%, 4%, 4.5% or 5% by weight of the total coating formulation. In a specific embodiment, medium chain triglycerides are present at an amount of about 2% by weight of the total coating formulation.

In one aspect of this embodiment, another excipient is polydextrose. In one embodiment, polydextrose is present at an amount of about 10% to about 60%, about 15% to about 50%, about 20% to about 40%, or about 25% to about 30% by weight of the total coating formulation. In another embodiment, polydextrose is present at an amount of about 5%, 10%, 15%, 20%, 25% or 30% by weight of the total coating formulation. In a specific embodiment, polydextrose is present at an amount of about 26% by weight of the total coating formulation.

In another aspect of this embodiment, another excipient is hypromellose. In one specific embodiment, hypromellose is hypromellose 15 cP. In one embodiment, hypromellose is present at an amount of about 10% to about 60%, about 15% to about 50%, about 25% to about 40%, or about 30% to about 35% by weight of the total coating formulation. In another embodiment, hypromellose is present at an amount of about 5%, 10%, 15%, 20%, 25%, 30% or 35% by weight of the total coating formulation. In a specific embodiment, hypromellose is present at an amount of about 31% by weight of the total coating formulation.

In another aspect of this embodiment, another excipient is talc. In one embodiment, talc is present at an amount of about 1% to about 20%, about 3% to about 15%, about 5% to about 10%, or about 5% to about 10% by weight of the total coating formulation. In another embodiment, talc is present at an amount of about 1%, 5%, 10%, 15% or 20% by weight of the total coating formulation. In a specific embodiment, talc is present at an amount of about 7% by weight of the total coating formulation.

In another aspect of this embodiment, another excipient is maltodextrin. In one embodiment, maltodextrin is present at an amount of about 0.1% to about 20%, about 0.5% to about 25%, about 1% to about 10%, or about 1% to about 5% by weight of the total coating formulation. In another embodiment, maltodextrin is present at an amount of about 1%, 2%, 3%, 4%, 5%, 6%, 7%, 8%, 9% or 10% by weight of the total coating formulation. In a specific embodiment, maltodextrin is present at an amount of about 5% by weight of the total coating formulation.

In another aspect of this embodiment, the excipients are one or more coloring agents. In one embodiment, the coloring agents are present at an amount of about 10% to about 60%, about 15% to about 50%, about 20% to about 40%, or about 25% to about 30% by weight of the total coating formulation. In another embodiment, the coloring agents are present at an amount of about 5%, 10%, 15%, 20%, 25% or 30% by weight of the total coating formulation. In a specific embodiment, the coloring agents are present at an amount of about 29% by weight of the total coating formulation.

In a specific embodiment, provided herein is a coating formulation comprising: polydextrose at an amount of about 26% by weight of the total coating formulation; hypromellose at an amount of about 31% by weight of the total coating formulation; talc at an amount of about 7% by weight of the total coating formulation; maltodextrin at an amount of about 5% by weight of the total coating formulation; medium chain triglycerides at an amount of about 2% by weight of the total coating formulation; and a mixture of coloring agents at an amount of about 29% of the total weight of the coating formulation.

In another embodiment where coating formulations contain medium chain triglycerides, medium chain triglycerides are present at an amount of about 0.1 to about 15%, about 0.5 to about 10%, about 1% to about 5%, or about 1% to 3% by weight of the total coating formulation. In another embodiment, medium chain triglycerides are present at an amount of about 0.1%, 0.5%, 1%, 1.5%, 2%, 2.5%, 3%, 3.5%, 4%, 4.5% or 5% by weight of the total coating formulation. In a specific embodiment, medium chain triglycerides are present at an amount of about 4% by weight of the total coating formulation.

In one aspect of this embodiment, another excipient is polydextrose. In one embodiment, polydextrose is present at an amount of about 1% to about 40%, about 5% to about 30%, about 10% to about 20%, or about 10% to about 15% by weight of the total coating formulation. In another embodiment, polydextrose is present at an amount of about 5%, 10%, 15%, 20%, 25% or 30% by weight of the total coating formulation. In a specific embodiment, polydextrose is present at an amount of about 13% by weight of the total coating formulation.

In another aspect of this embodiment, another excipient is hypromellose. In one specific embodiment, hypromellose is hypromellose 15 cP. In one embodiment, hypromellose is present at an amount of about 10% to about 65%, about 20% to about 60%, about 25% to about 50%, or about 35% to about 45% by weight of the total coating formulation. In another embodiment, hypromellose is present at an amount of about 10%, 15%, 20%, 25%, 30%, 35%, 40%, 45%, 50%, 55% or 60% by weight of the total coating formulation. In a specific embodiment, hypromellose is present at an amount of about 44% by weight of the total coating formulation.

In another aspect of this embodiment, another excipient is talc. In one embodiment, talc is present at an amount of about 1% to about 20%, about 3% to about 15%, about 5% to about 10%, or about 5% to about 10% by weight of the total coating formulation. In another embodiment, talc is present at an amount of about 1%, 5%, 10%, 15% or 20% by weight of the total coating formulation. In a specific embodiment, talc is present at an amount of about 7% by weight of the total coating formulation.

In another aspect of this embodiment, another excipient is maltodextrin. In one embodiment, maltodextrin is present at an amount of about 0.1% to about 20%, about 0.5% to about 25%, about 1% to about 10%, or about 1% to about 5% by weight of the total coating formulation. In another embodiment, maltodextrin is present at an amount of about 1%, 2%, 3%, 4%, 5%, 6%, 7%, 8%, 9% or 10% by weight of the total coating formulation. In a specific embodiment, maltodextrin is present at an amount of about 5% by weight of the total coating formulation.

In another aspect of this embodiment, the excipients are one or more coloring agents. In one embodiment, the coloring agents are present at an amount of about 10% to about 60%, about 15% to about 50%, about 20% to about 40%, or about 25% to about 30% by weight of the total coating formulation. In another embodiment, the coloring agents are present at an amount of about 5%, 10%, 15%, 20%, 25% or 30% by weight of the total coating formulation. In a specific embodiment, the coloring agents are present at an amount of about 27% by weight of the total coating formulation.

In a specific embodiment, provided herein is a coating formulation comprising: polydextrose at an amount of about 13% by weight of the total coating formulation; hypromellose at an amount of about 44% by weight of the total coating formulation; talc at an amount of about 7% by weight of the total coating formulation; maltodextrin at an amount of about 5% by weight of the total coating formulation; medium chain triglycerides at an amount of about 4% by weight of the total coating formulation; and a mixture of coloring agents at an amount of about 27% of the total weight of the coating formulation.

Any combination between core formulations and coating formulations provided herein can be used.

In one embodiment, provided herein is a formulation comprising Compound A or a pharmaceutically acceptable salt thereof; a filler; a disintegrant; and a lubricant, wherein compound A is present at an amount of about 5% to about 25% by weight of the total composition. In one aspect of this embodiment, the filler is lactose and is present at an amount of about 20% to 85% by weight of the total composition. In another aspect of this embodiment, the composition further comprises cellulose as a filler and is present at an amount of about 10% to about 50% by weight of the total composition. In another aspect of this embodiment, the disintegrant is croscarmellose and is present at an amount of about 2% to about 8% by weight of the total composition. In another aspect of this embodiment, the lubricant is magnesium stearate and is present at an amount of about 0.25% to about 5% of the total composition.

In one embodiment, the pharmaceutical composition is coated with a coating formulation, wherein the coating formulation comprises one or more excipients, wherein the excipient is polyvinyl alcohol and present at an amount of about 35% to about 45% by weight of the total coating formulation. In another embodiment the excipient is polyethylene glycol is present at an amount of about 20% to about 25% by weight of the total coating formulation. In another embodiment the excipient is talc and is present at an amount of about 10% to about 15% by weight of the total coating formulation. In another embodiment, the excipients are one or more coloring agents present at an amount of about 25% to about 30% by weight of the total coating formulation.

In a specific embodiment, provided herein is a formulation comprising (1) Compound A or a pharmaceutically acceptable salt thereof; at an amount of about 5% to about 25% by weight of the total composition; (2) lactose at an amount of about 20% to 85% by weight of the total composition; (3) cellulose at an amount of about 10% to about 50% by weight of the total composition; (4) croscarmellose at an amount of about 2% to about 8% by weight of the total composition; and (5) magnesium stearate at an amount of about 0.25% to about 5% of the total composition.

In a specific embodiment, the pharmaceutical composition is coated with a coating formulation, wherein the coating formulation comprises: (1) polyvinyl alcohol at an amount of about 35% to about 45% by weight of the total coating formulation; and/or (2) polyethylene glycol at an amount of about 20% to about 25% by weight of the total coating formulation; and/or (3) talc at an amount of about 10% to about 15% b y weight of the total coating formulation; and/or (4) one or more coloring agents at an amount of about 25% to about 30% by weight of the total coating formulation.

In a specific embodiment, provided herein is a formulation of Compound A, wherein the core formulation comprises the following:

Compound A at an amount of about 10% by weight of the total core composition; lactose at an amount of about 60% by weight of the total core composition; microcrystalline cellulose at an amount of about 26.25% by weight of the total core composition; croscarmellose at an amount of about 3% by weight of the total core composition; and magnesium stearate at an amount of about 0.75% by weight of the total core composition; and the coating formulation comprises the following:

polyvinyl alcohol at an amount of about 40% by weight of the total coating formulation; polyethylene glycol at an amount of about 20% by weight of the total coating formulation; talc at an amount of about 15% by weight of the total coating formulation; and a mixture of coloring agents at an amount of about 25% by weight of the total coating formulation.

Pharmaceutical compositions and formulations provided herein can be presented as discrete dosage forms. Although a preferred oral dosage unit form is in the form of a tablet, other forms of dosage forms can also be employed. For example, it is possible to use the core formulation in connection with other forms of dosage forms such as a capsule or a caplet. In some embodiments, the formulation is in the form of a tablet.

In some embodiments, because it is typical to obtain Compound A, or a pharmaceutically acceptable prodrug, salt, solvate, or clathrate thereof, at a purity of less than 100%, the formulations and dosage forms provided herein may be defined as compositions, formulations, or dosage forms that comprise Compound A, or a pharmaceutically acceptable prodrug, salt, solvate, or clathrate thereof, at an amount that provides the potency of a specified amount of 100% pure Compound A.

In certain embodiments, provided herein are anhydrous pharmaceutical compositions and dosage forms including an active ingredient, since water can facilitate the degradation of some compounds. For example, the addition of water (e.g., 5 percent) is widely accepted in the pharmaceutical arts as a means of simulating shelf-life, i.e., long-term storage in order to determine characteristics such as shelf-life or the stability of formulations over time. See, e.g., Jens T. Carstensen, *Drug Stability: Principles & Practice,* 2d. Ed., Marcel Dekker, NY, NY, 1995, pp. 379-80. In effect, water and heat accelerate decomposition. Thus, the effect of water on a formulation can be of great significance since moisture and/or humidity are commonly encountered during manufacture, handling, packaging, storage, shipment, and use of formulations.

An anhydrous pharmaceutical composition should be prepared and stored such that the anhydrous nature is maintained. Accordingly, in some embodiments, anhydrous compositions are packaged using materials known to prevent exposure to water such that they can be included in suitable formulary kits. Examples of suitable packaging include, but are not limited to, hermetically sealed foils, plastic or the like, unit dose containers, blister packs, and strip packs.

In this regard, also provided herein is a method of preparing a solid pharmaceutical formulation including an active ingredient through admixing the active ingredient and an excipient under anhydrous or low moisture/humidity conditions, wherein the ingredients are substantially free of water. The method can further include packaging the anhydrous or non-hygroscopic solid formulation under low moisture conditions. By using such conditions, the risk of contact with water is reduced and the degradation of the active ingredient can be prevented or substantially reduced.

4.1.1. Second Active Agents

In certain embodiments, provided herein are compositions and dosage forms of Compound A, or a pharmaceutically acceptable prodrug, salt, solvate, or clathrate thereof, which may further comprise one or more secondary active ingredients. Certain combinations may work synergistically in the treatment of particular types of diseases or disorders, and conditions and symptoms associated with such diseases or disorders. Compound A, or a pharmaceutically acceptable prodrug, salt, solvate, or clathrate thereof, can also work to alleviate adverse effects associated with certain second active agents, and vice versa.

Specific second active compounds that can be contained in the formulations and dosage forms provided herein vary depending on the specific indication to be treated, prevented or managed.

For instance, for the treatment, prevention or management of cancer, second active agents include, but are not limited to: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Yet other second active agents include, but are not limited to, 2-methoxyestradiol, telomestatin, inducers of apoptosis in multiple myeloma cells (such as, for example, TRAIL), statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

In another embodiment, examples of specific second agents according to the indications to be treated, prevented, or managed can be found in the following references, all of which are incorporated herein in their entireties: U.S. Pat. Nos. 6,281,230 and 5,635,517; U.S. publication nos. 2004/0220144, 2004/0190609, 2004/0087546, 2005/0203142, 2004/0091455, 2005/0100529, 2005/0143344, 2005/0214328, 2005/0239842, 2006/0122228, 2006/0154880 and 2006/0188475.

Examples of second active agents that may be used for the treatment, prevention and/or management of pain include, but are not limited to, conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the *Physician's Desk Reference* 2003. Specific examples include, but are not limited to, salicylic acid acetate (Aspirin®), celecoxib (Celebrex®), Enbrel®, ketamine, gabapentin (Neurontin®), phenytoin (Dilantin®), carbamazepine (Tegretol®), oxcarbazepine (Trileptal®), valproic acid (Depakene®), morphine sulfate, hydromorphone, prednisone, griseofulvin, penthonium, alendronate, dyphenhydramide, guanethidine, ketorolac (Acular®), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac®), sertraline (Zoloft®), naproxen, nefazodone (Serzone®), venlafaxine (Effexor®), trazodone (Desyrel®), bupropion (Wellbutrin®), mexiletine, nifedipine, propranolol, tramadol, lamotrigine, vioxx, ziconotide, ketamine, dextromethorphan, benzodiazepines, baclofen, tizanidine and phenoxybenzamine.

Examples of second active agents that may be used for the treatment, prevention and/or management of macular degeneration and related syndromes include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof. Specific examples include, but are not limited to, verteporfin, purlytin, an angiostatic steroid, rhuFab, interferon-2α, pentoxifylline, tin etiopurpurin, motexafin, lucentis, lutetium, 9-fluoro-11,21-dihydroxy-16, 17-1-methylethylidinebis (oxy)pregna-1,4-diene-3,20-dione, latanoprost (see U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-O-Mal genistin, 6'-O-Ac genistin, daidzein, daidzin, 6'-O-Mal daidzin, 6'-O-Ac daidzin, glycitein, glycitin, 6'-O-Mal glycitin, biochanin A, formononetin (U.S. Pat. No. 6,001,368), triamcinolone acetomide, dexamethasone (U.S. Pat. No. 5,770,589), thalidomide, glutathione (U.S. Pat. No. 5,632,984), basic fibroblast growth factor (bFGF), transforming growth factor b (TGF-b), brain-derived neurotrophic factor (BDNF), plasminogen activator factor type 2 (PAI-2), EYE101 (Eyetech Pharmaceuticals), LY333531 (Eli Lilly), Miravant, and RETISERT implant (Bausch & Lomb). All of the references cited herein are incorporated in their entireties by reference.

Examples of second active agents that may be used for the treatment, prevention and/or management of skin diseases include, but are not limited to, keratolytics, retinoids, α-hydroxy acids, antibiotics, collagen, botulinum toxin, interferon, steroids, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

Examples of second active agents that may be used for the treatment, prevention and/or management of pulmonary hypertension and related disorders include, but are not limited to, anticoagulants, diuretics, cardiac glycosides, calcium channel blockers, vasodilators, prostacyclin analogues, endothelin antagonists, phosphodiesterase inhibitors (e.g., PDE V inhibitors), endopeptidase inhibitors, lipid lowering agents, thromboxane inhibitors, and other therapeutics known to reduce pulmonary artery pressure. Specific examples include, but are not limited to, warfarin (Coumadin®), a diuretic, a cardiac glycoside, digoxin-oxygen, diltiazem, nifedipine, a vasodilator such as prostacyclin (e.g., prostaglandin I2 (PGI2), epoprostenol (EPO, Floran®), treprostinil (Remodulin®), nitric oxide (NO), bosentan (Tracleer®), amlodipine, epoprostenol (Floran®), treprostinil (Remodulin®), prostacyclin, tadalafil (Cialis®), simvastatin (Zocor®), omapatrilat (Vanlev®), irbesartan (Avapro®), pravastatin (Pravachol®), digoxin, L-arginine, iloprost, betaprost, and sildenafil (Viagra®).

Examples of second active agents that may be used for the treatment, prevention and/or management of asbestos-related disorders include, but are not limited to, anthracycline, platinum, alkylating agent, oblimersen (Genasense®), cisplatinum, cyclophosphamide, temodar, carboplatin, procarbazine, gliadel, tamoxifen, topotecan, methotrexate, taxotere, irinotecan, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, bleomycin, hyaluronidase, mitomycin C, mepacrine, thiotepa, tetracycline and gemcitabine.

Examples of second active agents that may be used for the treatment, prevention and/or management of parasitic diseases include, but are not limited to, chloroquine, quinine, quinidine, pyrimethamine, sulfadiazine, doxycycline, clindamycin, mefloquine, halofantrine, primaquine, hydroxychloroquine, proguanil, atovaquone, azithromycin, suramin, pentamidine, melarsoprol, nifurtimox, benznidazole, amphotericin B, pentavalent antimony compounds (e.g., sodium stiboglucuronate), interfereon gamma, itraconazole, a combination of dead promastigotes and BCG, leucovorin, corticosteroids, sulfonamide, spiramycin, IgG (serology), trimethoprim, and sulfamethoxazole.

Examples of second active agents that may be used for the treatment, prevention and/or management of immunodeficiency disorders include, but are not limited to: antibiotics (therapeutic or prophylactic) such as, but not limited to, ampicillin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levami sole and isoprinosine; biologics such as, but not limited to, gammaglobulin, transfer factor, interleukins, and interferons; hormones such as, but not limited to, thymic; and other immunologic agents such as, but not limited to, B cell stimulators (e.g., BAFF/BlyS), cytokines (e.g., IL-2, IL-4, and IL-5), growth factors (e.g., TGF-α), antibodies (e.g., anti-CD40 and IgM), oligonucleotides containing unmethylated CpG motifs, and vaccines (e.g., viral and tumor peptide vaccines).

Examples of second active agents that may be used for the treatment, prevention and/or management of CNS disorders include, but are not limited to: opioids; a dopamine agonist or antagonist, such as, but not limited to, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, and Symmetrel; a MAO inhibitor, such as, but not limited to, iproniazid, clorgyline, phenelzine and isocarboxazid; a COMT inhibitor, such as, but not limited to, tolcapone and entacapone; a cholinesterase inhibitor, such as, but not limited to, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, and demecarium; an anti-inflammatory agent, such as, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone or betamethasone and other glucocorticoids; and an antiemetic agent, such as, but not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinol, thiethylperazine, thioproperazine, tropisetron, and a mixture thereof.

Examples of second active agents that may be used for the treatment, prevention and/or management of CNS injuries and related syndromes include, but are not limited to, immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in patients with CNS injury/damage and related syndromes. Specific examples include, but are not limited to: steroids (e.g., glucocorticoids, such as, but not limited to, methylprednisolone, dexamethasone and betamethasone); an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone; a cAMP analog including, but not limited to, db-cAMP; an agent comprising a methylphenidate drug, which comprises 1-threo-methylphenidate, d-threo-methylphenidate, dl-threo-methylphenidate, 1-erythro-methylphenidate, d-erythro-methylphenidate, dl-erythro-methylphenidate, and a mixture thereof; and a diuretic agent such as, but not limited to, mannitol, furosemide, glycerol, and urea.

Examples of second active agent that may be used for the treatment, prevention and/or management of dysfunctional sleep and related syndromes include, but are not limited to, a tricyclic antidepressant agent, a selective serotonin reuptake inhibitor, an antiepileptic agent (gabapentin, pregabalin, carbamazepine, oxcarbazepine, levitiracetam, topiramate), an antiaryhthmic agent, a sodium channel blocking agent, a selective inflammatory mediator inhibitor, an opioid agent, a second immunomodulatory compound, a combination agent, and other known or conventional agents used in sleep therapy. Specific examples include, but are not limited to, Neurontin, oxycontin, morphine, topiramate, amitryptiline, nortryptiline, carbamazepine, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, Symmetrel, iproniazid, clorgyline, phenelzine, isocarboxazid, tolcapone, entacapone, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, demecarium, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone, benzbromarone, betamethasone and other glucocorticoids, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of second active agents that may be used for the treatment, prevention and/or management of hemoglobinopathy and related disorders include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; and G-CSF; hydroxyurea; butyrates or butyrate derivatives; nitrous oxide; hydroxy urea; HEMOXIN™ (NIPRISAN™; see U.S. Pat. No. 5,800,819); Gardos channel antagonists such as clotrimazole and triaryl methane derivatives; Deferoxamine; protein C; and transfusions of blood, or of a blood substitute such as Hemospan™ or Hemospan™ PS (Sangart).

4.2. Process for Making Dosage Forms

Dosage forms provided herein can be prepared by any of the methods of pharmacy, but all methods include the step of bringing the active ingredient into association with the excipient, which constitutes one or more necessary ingredients. In general, the compositions are prepared by uniformly admixing (e.g., direct blend) the active ingredient with liquid excipients or finely divided solid excipients or both, and then, if necessary, shaping the product into the desired presentation (e.g., compaction such as roller-compaction). If desired, tablets can be coated by standard aqueous or non-aqueous techniques.

A dosage form provided herein can be prepared by compression or molding, optionally with one or more accessory ingredients. Compressed tablets can be prepared by compressing in a suitable machine the active ingredient in a free-flowing form such as powder or granules, optionally mixed with an excipient as above and/or a surface active or dispersing agent. Molded tablets can be made by molding in a suitable machine a mixture of the powdered compound moistened with an inert liquid diluent. Encapsulation of the dosage forms provided herein can be done using capsules of methylcellulose, calcium alginate, or gelatin.

In some embodiments, the active ingredients and excipients are directly blended and loaded into, for example, a capsule, or compressed directly into tablets. A direct-blended dosage form may be more advantageous than a compacted (e.g., roller-compacted) dosage form in certain instances, since direct-blending can reduce or eliminate the harmful health effects that may be caused by airborne particles of ingredients during the manufacture using compaction process.

Direct blend formulations may be advantageous in certain instances because they require only one blending step, that of the active and excipients, before being processed into the final dosage form, e.g., tablet or capsule. This can reduce the production of airborne particle or dust to a minimum, while roller-compaction processes may be prone to produce dust. In roller-compaction process, the compacted material is often milled into smaller particles for further processing. The milling operation can produce significant amounts of airborne particles, since the purpose for this step in manufacturing is to reduce the materials particle size. The milled material is then blended with other ingredients prior to manufacturing the final dosage form.

For certain active ingredients, in particular for a compound with a low solubility, the active ingredient's particle size is reduced to a fine powder in order to help increase the active ingredient's rate of solubilization. The increase in the rate of solubilization is often necessary for the active ingredient to be effectively absorbed in the gastrointestinal tract. However for fine powders to be directly-blended and loaded onto capsules, the excipients should preferably provide certain characteristics which render the ingredients suitable for the direct-blend process. Examples of such characteristics include, but are not limited to, acceptable flow characteristics. In one embodiment, therefore, provided herein is the use of, and compositions comprising, excipients which may provide characteristics, which render the resulting mixture suitable for direct-blend process, e.g., good flow characteristics. In certain embodiments, a dry blend tablet formulation is the preferred way of making the tablets provided herein.

4.2.1. Screening

The process for making the pharmaceutical compositions of the invention preferably includes the screening of the active ingredient and the excipient(s). In one embodiment, the active ingredient is passed through a screen having openings of about 200 microns to about 750 microns. In another embodiment, the active ingredient is passed through a screen with openings of about 200 microns to about 400 microns. In one embodiment, the active ingredient is passed through a screen having openings of about 300 to about 400 microns. Depending on the excipient(s) used, the screen openings vary. For example, disintegrants and binders are passed through openings of about 430 microns to about 750 microns, from about 600 microns to about 720 microns, or about 710 microns. Lubricants are typically passed through smaller openings, e.g., about 150 microns to about 250 microns screen. In one embodiment, the lubricant is passed through a screen opening of about 210 microns.

4.2.2. Pre-Blending

After the ingredients are screened, the excipient and active ingredient are mixed in a diffusion mixer. In one embodiment, the mixing time is from about 1 minute to about 50 minutes, from about 5 minutes to about 45 minutes, from about 10 minutes to about 40 minutes, or from about 10 minutes to about 25 minutes. In another embodiment, the mixing time is about 15 minutes.

When more than one excipient is used, the excipients may be admixed in a tumble blender for about 1 minute to about 20 minutes, or for about 5 minutes to about 10 minutes, prior to mixing with the active ingredient.

4.2.3. Roller Compaction

In one embodiment, the pre-blend may optionally be passed through a roller compactor with a hammer mill attached at the discharge of the compactor.

4.2.4. Final Blend

When a lubricant, e.g., sodium stearyl fumarate and magnesium stearate, is used, the lubricant is mixed with the pre-blend at the end of the process to complete the pharmaceutical composition. This additional mixing is from about 1 minute to about 10 minutes, or from about 3 minutes to about 5 minutes.

4.2.5. Tableting

The formulation mixture can be tableted (e.g., via compaction, compression, or molding) into the desired size and shape tablet using, for example, a tablet press or other conventional tableting equipment and standard techniques.

4.2.6. Encapsulation

The formulation mixture can also be optionally encapsulated into the desired size capsule shell using, for example, a capsule filling machine or a rotary tablet press.

4.3. Kits

Pharmaceutical packs or kits which comprise pharmaceutical compositions or dosage forms provided herein are also provided. An example of a kit comprises notice in the form prescribed by a governmental agency regulating the manufacture, use or sale of pharmaceuticals or biological products, which notice reflects approval by the agency of manufacture, use or sale for human administration.

4.4. Methods of Treatment, Prevention, and Management

Provided herein are methods of treating, preventing, and/or managing certain diseases or disorders using the formulations, compositions, or dosage forms provided herein.

Examples of diseases or disorders include, but are not limited to, those disorders related to PDE4, TNFα, cAMP and/or angiogenesis and include diseases or disorders such as various inflammatory diseases, pulmonary diseases, autoimmune diseases and immunological diseases. Specific examples include, but are not limited to, inflammation and various forms thereof, cancer, disorders associated with angiogenesis, pain including, but not limited to, Complex Regional Pain Syndrome ("CRPS"), Macular Degeneration ("MD") and related syndromes, skin diseases, pulmonary disorders, asbestos-related disorders, parasitic diseases, immunodeficiency disorders, CNS disorders, CNS injury, atherosclerosis and related disorders, dysfunctional sleep and related disorders, hemoglobinopathy and related disorders (e.g., anemia), tuberculosis and related disorders, PDE4/TNFα related disorders, infectious diseases, and other various diseases and disorders.

In one embodiment, exemplary diseases or disorders include, but are not limited to, inflammatory, viral, genetic, allergic, skin, and autoimmune diseases. Specific examples include, but are not limited to, arthritis, HIV, hepatitis, acne, adult respiratory distress syndrome, bone resorption diseases, chronic pulmonary inflammatory diseases, dermatitis, dematomyositis, cystic fibrosis, Lichen Planus, septic shock, sepsis, endotoxic shock, hemodynamic shock, sepsis syndrome, post ischemic reperfusion injury, meningitis, psoriasis, fibrotic disease, cachexia, graft versus host disease, graft rejection, auto-immune disease, rheumatoid spondylitis, Behcet disease, dermatitis, Crohn's disease, ulcerative colitis, inflammatory-bowel disease, rosacea, multiple sclerosis, systemic lupus erythrematosus, ENL in leprosy, sarcoidosis, radiation damage, cancer, asthma, uveitis, or hyperoxic alveolar injury.

In one embodiment, the disease is psoriasis. In another embodiment, psoriasis is plaque psoriasis.

In another embodiment, the disease is arthritis. In another embodiment, arthritis is psoriatic arthritis, rheumatoid arthritis, osteoarthritis or acute gouty arthritis.

In another embodiment, the disease is a skin disease. In another embodiment, skin disease is acne, dermatitis or dermatomyositis. In another embodiment, dermatitis is atopic dermatitis or contact dermatitis.

In another embodiment, the disease is ulcerative colitis.

In another embodiment, the disease is Behcet's disease.

In another embodiment, the disease is Crohn's disease.

In another embodiment, the disease is sarcoidosis. In another embodiment, sarcoidosis is chronic cutaneous sarcoidosis.

In another embodiment, the disease is uveitis.

In another embodiment, the disease is rosacea.

In another embodiment, the disease is Lichen Planus.

In other embodiments, provided herein are methods of treating, preventing and/or managing various other diseases or disorders using the compositions and formulations provided herein. Examples of other diseases or disorders are provided in the following.

Examples of cancer and precancerous conditions include, but are not limited to, those described in U.S. Pat. Nos. 6,281,230 and 5,635,517 to Muller et al., in various U.S. patent publications to Zeldis, including publication nos. 2004/0220144A1, published Nov. 4, 2004 (Treatment of Myelodysplastic Syndrome); 2004/0029832A1, published Feb. 12, 2004 (Treatment of Various Types of Cancer); and 2004/0087546, published May 6, 2004 (Treatment of Myeloproliferative Diseases). Examples also include those described in WO 2004/103274, published Dec. 2, 2004. All of these references are incorporated herein in their entireties by reference.

Certain examples of cancer include, but are not limited to, cancers of the skin, such as melanoma; lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. The compounds are also useful for treating cancers of the blood and bone marrow, such as multiple myeloma and acute and chronic leukemias, for example, lymphoblastic, myelogenous, lymphocytic, and myelocytic leukemias. The compounds provided herein can be used for treating, preventing or managing either primary or metastatic tumors.

Other cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, chronic lymphocytic leukemia (CLL), Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistance to chemotherapy or radiation.

In one embodiment, the diseases or disorders are various forms of leukemias such as chronic lymphocytic leukemia, chronic myelocytic leukemia, acute lymphoblastic leukemia, acute myelogenous leukemia and acute myeloblastic leukemia, including leukemias that are relapsed, refractory or resistant, as disclosed in U.S. publication no. 2006/0030594, published Feb. 9, 2006, which is incorporated in its entirety by reference.

The term "leukemia" refers malignant neoplasms of the blood-forming tissues. The leukemia includes, but is not limited to, chronic lymphocytic leukemia, chronic myelocytic leukemia, acute lymphoblastic leukemia, acute myelogenous leukemia and acute myeloblastic leukemia. The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow.

In another embodiment, the diseases or disorders are various types of lymphomas, including Non-Hodgkin's lymphoma (NHL). The term "lymphoma" refers a heterogenous group of neoplasms arising in the reticuloendothelial and lymphatic systems. "NHL" refers to malignant monoclonal proliferation of lymphoid cells in sites of the immune system, including lymph nodes, bone marrow, spleen, liver and gastrointestinal tract. Examples of NHL include, but are not limited to, mantle cell lymphoma (MCL), lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), follicular lymphoma, and any type of the mantle cell lymphomas that can be seen under the microscope (nodular, diffuse, blastic and mentle zone lymphoma).

Examples of diseases and disorders associated with, or characterized by, undesired angiogenesis include, but are not limited to, inflammatory diseases, autoimmune diseases, viral diseases, genetic diseases, allergic diseases, bacterial diseases, ocular neovascular diseases, choroidal neovascular diseases, retina neovascular diseases, and rubeosis (neovascularization of the angle). Specific examples of the diseases and disorders associated with, or characterized by, undesired angiogenesis include, but are not limited to, arthritis, endometriosis, Crohn's disease, heart failure, advanced heart failure, renal impairment, endotoxemia, toxic shock syndrome, osteoarthritis, retrovirus replication, wasting, meningitis, silica-induced fibrosis, asbestos-induced fibrosis, veterinary disorder, malignancy-associated hypercalcemia, stroke, circulatory shock, periodontitis, gingivitis, macrocytic anemia, refractory anemia, and 5q-deletion syndrome.

Examples of pain include, but are not limited to those described in U.S. patent publication no. 2005/0203142, published Sep. 15, 2005, which is incorporated herein by reference. Specific types of pain include, but are not limited to, nociceptive pain, neuropathic pain, mixed pain of nociceptive and neuropathic pain, visceral pain, migraine, headache and post-operative pain.

Examples of nociceptive pain include, but are not limited to, pain associated with chemical or thermal burns, cuts of the skin, contusions of the skin, osteoarthritis, rheumatoid arthritis, tendonitis, and myofascial pain.

Examples of neuropathic pain include, but are not limited to, CRPS type I, CRPS type II, reflex sympathetic dystrophy (RSD), reflex neurovascular dystrophy, reflex dystrophy, sympathetically maintained pain syndrome, causalgia, Sudeck atrophy of bone, algoneurodystrophy, shoulder hand syndrome, post-traumatic dystrophy, trigeminal neuralgia, post herpetic neuralgia, cancer related pain, phantom limb pain, fibromyalgia, chronic fatigue syndrome, spinal cord injury pain, central post-stroke pain, radiculopathy, diabetic neuropathy, post-stroke pain, luetic neuropathy, and other painful neuropathic conditions such as those induced by drugs such as vincristine and velcade.

As used herein, the terms "complex regional pain syndrome," "CRPS" and "CRPS and related syndromes" mean a chronic pain disorder characterized by one or more of the following: pain, whether spontaneous or evoked, including allodynia (painful response to a stimulus that is not usually painful) and hyperalgesia (exaggerated response to a stimulus that is usually only mildly painful); pain that is disproportionate to the inciting event (e.g., years of severe pain after an ankle sprain); regional pain that is not limited to a single peripheral nerve distribution; and autonomic dysregulation (e.g., edema, alteration in blood flow and hyperhidrosis) associated with trophic skin changes (hair and nail growth abnormalities and cutaneous ulceration).

Examples of MD and related syndromes include, but are not limited to, those described in U.S. patent publication no. 2004/0091455, published May 13, 2004, which is incorporated herein by reference. Specific examples include, but are not limited to, atrophic (dry) MD, exudative (wet) MD, age-related maculopathy (ARM), choroidal neovascularisation (CNVM), retinal pigment epithelium detachment (PED), and atrophy of retinal pigment epithelium (RPE).

Examples of skin diseases include, but are not limited to, those described in U.S. publication no. 2005/0214328A1, published Sep. 29, 2005, which is incorporated herein by reference. Specific examples include, but are not limited to, keratoses and related symptoms, skin diseases or disorders characterized with overgrowths of the epidermis, acne, and wrinkles.

As used herein, the term "keratosis" refers to any lesion on the epidermis marked by the presence of circumscribed overgrowths of the horny layer, including but not limited to actinic keratosis, seborrheic keratosis, keratoacanthoma, keratosis follicularis (Darier disease), inverted follicular keratosis, palmoplantar keratoderma (PPK, keratosis palmaris et plantaris), keratosis pilaris, and stucco keratosis. The term "actinic keratosis" also refers to senile keratosis, keratosis senilis, verruca senilis, plana senilis, solar keratosis, keratoderma or keratoma. The term "seborrheic keratosis" also refers to seborrheic wart, senile wart, or basal cell papilloma. Keratosis is characterized by one or more of the following symptoms: rough appearing, scaly, erythematous papules, plaques, spicules or nodules on exposed surfaces (e.g., face, hands, ears, neck, legs and thorax), excrescences of keratin referred to as cutaneous horns, hyperkeratosis, telangiectasias, elastosis, pigmented lentigines, acanthosis, parakeratosis, dyskeratoses, papillomatosis, hyperpigmentation of the basal cells, cellular atypia, mitotic figures, abnormal cell-cell adhesion, dense inflammatory infiltrates and small prevalence of squamous cell carcinomas.

Examples of skin diseases or disorders characterized with overgrowths of the epidermis include, but are not limited to, any conditions, diseases or disorders marked by the presence of overgrowths of the epidermis, including but not limited to, infections associated with papilloma virus, arsenical keratoses, sign of Leser-Trélat, warty dyskeratoma (WD), trichostasis spinulosa (TS), erythrokeratodermia variabilis (EKV), ichthyosis fetalis (harlequin ichthyosis), knuckle pads, cutaneous melanoacanthoma, porokeratosis, psoriasis, squamous cell carcinoma, confluent and reticulated papillomatosis (CRP), acrochordons, cutaneous horn, cowden disease (multiple hamartoma syndrome), dermatosis papulosa nigra (DPN), epidermal nevus syndrome (ENS), ichthyosis vulgaris, molluscum contagiosum, prurigo nodularis, and acanthosis nigricans (AN).

Examples of pulmonary disorders include, but are not limited to, those described in U.S. publication no. 2005/0239842A1, published Oct. 27, 2005, which is incorporated herein by reference. Specific examples include pulmonary hypertension and related disorders. Examples of pulmonary hypertension and related disorders include, but are not limited to: primary pulmonary hypertension (PPH); secondary pulmonary hypertension (SPH); familial PPH; sporadic PPH; precapillary pulmonary hypertension; pulmonary arterial hypertension (PAH); pulmonary artery hypertension; idiopathic pulmonary hypertension; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vascular disease, congenital heart disease, HIV virus infection, drugs and toxins such as fenfluramines, congenital heart disease, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus including systemic and cutaneous lupus, schistosomiasis, sarcoidosis or pulmonary capillary hemangiomatosis.

Examples of asbestos-related disorders include, but not limited to, those described in U.S. publication no. 2005/0100529, published May 12, 2005, which is incorporated herein by reference. Specific examples include, but are not limited to, mesothelioma, asbestosis, malignant pleural effusion, benign exudative effusion, pleural plaques, pleural calcification, diffuse pleural thickening, rounded atelectasis, fibrotic masses, and lung cancer.

Examples of parasitic diseases include, but are not limited to, those described in U.S. publication no. 2006/0154880, published Jul. 13, 2006, which is incorporated herein by reference. Parasitic diseases include diseases and disorders caused by human intracellular parasites such as, but not limited to, *P. falcifarium, P. ovale, P. vivax, P. malariae, L. donovari, L. infantum, L. aethiopica, L. major, L. tropica, L. mexicana, L. braziliensis, T. Gondii, B. microti, B. divergens, B. coli, C. parvum, C. cayetanensis, E. histolytica, I. belli, S. mansonii, S. haematobium, Trypanosoma* ssp., *Toxoplasma* ssp., and *O. volvulus*. Other diseases and disorders caused by non-human intracellular parasites such as, but not limited to, *Babesia bovis, Babesia canis, Banesia gibsoni, Besnoitia darlingi, Cytauxzoon felis, Eimeria* ssp., *Hammondia* ssp., and *Theileria* ssp., are also encompassed. Specific examples include, but are not limited to, malaria, babesiosis, trypanosomiasis, leishmaniasis, toxoplasmosis, meningoencephalitis, keratitis, amebiasis, giardiasis, cryptosporidiosis, isosporiasis, cyclosporiasis, microsporidiosis, ascariasis, trichuriasis, ancylostomiasis, strongyloidiasis, toxocariasis, trichinosis, lymphatic filariasis, onchocerciasis, filariasis, schistosomiasis, and dermatitis caused by animal schistosomes.

Examples of immunodeficiency disorders include, but are not limited to, those described in U.S. publication no. 2006/0188475, published Aug. 24, 2006. Specific examples include, but not limited to, adenosine deaminase deficiency, antibody deficiency with normal or elevated Igs, ataxia-tenlangiectasia, bare lymphocyte syndrome, common variable immunodeficiency, Ig deficiency with hyper-IgM, Ig heavy chain deletions, IgA deficiency, immunodeficiency with thymoma, reticular dysgenesis, Nezelof syndrome, selective IgG subclass deficiency, transient hypogammaglobulinemia of infancy, Wistcott-Aldrich syndrome, X-linked agammaglobulinemia, X-linked severe combined immunodeficiency.

Examples of CNS disorders include, but are not limited to, those described in U.S. publication no. 2005/0143344, published Jun. 30, 2005, which is incorporated herein by reference. Specific examples include, but are not limited to, include, but are not limited to, Amyotrophic Lateral Sclerosis, Alzheimer Disease, Parkinson Disease, Huntington's Disease, Multiple Sclerosis other neuroimmunological disorders such as Tourette Syndrome, delerium, or disturbances in consciousness that occur over a short period of time, and amnestic disorder, or discreet memory impairments that occur in the absence of other central nervous system impairments.

Examples of CNS injuries and related syndromes include, but are not limited to, those described in U.S. publication no. 2006/0122228, published Jun. 8, 2006, which is incorporated herein by reference. Specific examples include, but are not limited to, CNS injury/damage and related syndromes, include, but are not limited to, primary brain injury, secondary brain injury, traumatic brain injury, focal brain injury, diffuse axonal injury, head injury, concussion, post-concussion syndrome, cerebral contusion and laceration, subdural hematoma, epidermal hematoma, post-traumatic epilepsy, chronic vegetative state, complete SCI, incomplete SCI, acute SCI, subacute SCI, chronic SCI, central cord syndrome, Brown-Sequard syndrome, anterior cord syndrome, conus medullaris syndrome, cauda equina syndrome, neurogenic shock, spinal shock, altered level of consciousness, headache, nausea, emesis, memory loss, dizziness, diplopia, blurred vision, emotional lability, sleep disturbances, irritability, inability to concentrate, nervousness, behavioral impairment, cognitive deficit, and seizure.

Examples of atherosclerosis and related conditions include, but are not limited to, those disclosed in U.S. publication no. 2002/0054899, published May 9, 2002, which is incorporated herein by reference. Specific examples include, but are not limited to, all forms of conditions involving atherosclerosis, including restenosis after vascular intervention such as angioplasty, stenting, atherectomy and grafting. All forms of vascular intervention are contemplated herein, including diseases of the cardiovascular and renal system, such as, but not limited to, renal angioplasty, percutaneous coronary intervention (PCI), percutaneous transluminal coronary angioplasty (PTCA), carotid percutaneous transluminal angioplasty (PTA), coronary by-pass grafting, angioplasty with stent implantation, peripheral percutaneous transluminal intervention of the iliac, femoral or popliteal arteries, and surgical intervention using impregnated artificial grafts. The following chart provides a listing of the major systemic arteries that may be in need of treatment, all of which are contemplated herein:

| Artery | Body Areas Supplied |
|---|---|
| Axillary | Shoulder and axilla |
| Brachial | Upper arm |
| Brachiocephalic | Head, neck, and arm |
| Celiac | Divides into left gastric, splenic, and hepatic arteries |
| Common carotid | Neck |
| Common iliac | Divides into external and internal iliac arteries |
| Coronary | Heart |
| Deep femoral | Thigh |
| Digital | Fingers |
| Dorsalis pedis | Foot |
| External carotid | Neck and external head regions |
| External iliac | Femoral artery |
| Femoral | Thigh |
| Gastric | Stomach |
| Hepatic | Liver, gallbladder, pancreas, and duodenum |
| Inferior mesenteric | Descending colon, rectum, and pelvic wall |
| Internal carotid | Neck and internal head regions |
| Internal iliac | Rectum, urinary bladder, external genitalia, buttocks muscles, uterus and vagina |
| Left gastric | Esophagus and stomach |
| Middle sacral | Sacrum |
| Ovarian | Ovaries |
| Palmar arch | Hand |
| Peroneal | Calf |
| Popliteal | Knee |
| Posterior tibial | Calf |
| Pulmonary | Lungs |
| Radial | Forearm |
| Renal | Kidney |
| Splenic | Stomach, pancreas, and spleen |
| Subclavian | Shoulder |
| Superior mesenteric | Pancreas, small intestine, ascending and transverse colon |
| Testicular | Testes |
| Ulnar | Forearm |

Examples of dysfunctional sleep and related syndromes include, but are not limited to, those disclosed in U.S. publication no. 2005/0222209A1, published Oct. 6, 2005, which is incorporated herein by reference. Specific examples include, but are not limited to, snoring, sleep apnea, insomnia, narcolepsy, restless leg syndrome, sleep terrors, sleep walking sleep eating, and dysfunctional sleep associated with chronic neurological or inflammatory conditions. Chronic neurological or inflammatory conditions, include, but are not limited to, Complex Regional Pain Syndrome, chronic low back pain, musculoskeletal pain, arthritis, radiculopathy, pain associated with cancer, fibromyalgia, chronic fatigue syndrome, visceral pain, bladder pain, chronic pancreatitis, neuropathies (diabetic, post-herpetic, traumatic or inflammatory), and neurodegenerative disorders such as Parkinson's Disease, Alzheimer's Disease, amyotrophic lateral sclerosis, multiple sclerosis, Huntington's Disease, bradykinesia; muscle rigidity; parkinsonian tremor; parkinsonian gait; motion freezing; depression; defective long-term memory, Rubinstein-Taybi syndrome (RTS); dementia; postural instability; hypokinetic disorders; synuclein disorders; multiple system atrophies; striatonigral degeneration; olivopontocerebellar atrophy; Shy-Drager syndrome; motor neuron disease with parkinsonian features; Lewy body dementia; Tau pathology disorders; progressive supranuclear palsy; corticobasal degeneration; frontotemporal dementia; amyloid pathology disorders; mild cognitive impairment; Alzheimer disease with parkinsonism; Wilson disease; Hallervorden-Spatz disease; Chediak-Hagashi disease; SCA-3 spinocerebellar ataxia; X-linked dystonia parkinsonism; prion disease; hyperkinetic disorders; chorea; ballismus; dystonia tremors; Amyotrophic Lateral Sclerosis (ALS); CNS trauma and myoclonus.

Examples of hemoglobinopathy and related disorders include, but are not limited to, those described in U.S. publication no. 2005/0143420A1, published Jun. 30, 2005, which is incorporated herein by reference. Specific examples include, but are not limited to, hemoglobinopathy, sickle cell anemia, and any other disorders related to the differentiation of CD34+ cells.

Examples of tuberculosis (TB) and related disorders include, but are not limited to, those described in PCT publication no. WO 2010/093588, published Feb. 9, 2010, which is incorporated herein by reference. Specific examples include, but are not limited to, pulmonary TB and extrapulmonary TB (remote TB lesions) such as, but not limited to, genitourinary TB (e.g., kidney TB), tubeculous meningitis, military TB, tuberculous peritonitis, tuberculous pericarditis, tuberculous lymphadentitis, TB of bones and joints, gastrointestinal TB, and TB of the liver. In certain embodiments, provided herein are methods of treating, preventing, and/or managing the symptoms associated with TB. Examples include, but are not limited to, cough, dyspnea, hilar lymphadenopathy, segmental atelectasis, swelling of the nodes, lobar atelectasis, pulmonary caviation, fever, unremitting headache, nausea, drowsiness, stupor, coma, stiff neck, weakness, and malaise.

Disorders related to TB often include other mycobacterial infections, symptom of which resemble those of TB. Examples of such disorders include, but are not limited to, disorders caused by *M. avium* complex (MAC; *M. avium* and *M. intracellulare*), *M. kansasii, M. xenopy, M. marinum, M. ulcerans, M. leprae*, and *M. fortuitum* complex (*M. fortuitum* and *M. chelonei*). Examples of disorders caused by these mycobacteria include, but are not limited to, pulmonary diseases, lymphadenitis, cutaneous diseases, wounds, and foreign body infections. In certain embodiments, treatment, prevention and/or management of other granulomatous diseases are also encompassed herein. Examples of such diseases include, but are not limited to: infectious agents caused diseases such as histoplasmosis, cryptococcus, schitosomiasis, and leishmaniasis; allergic reactions caused diseases such as berylliosis; non-infectious agents caused diseases such as aspiration pneumonia and foreign body reaction; genetically caused diseases such as chronic granulomatous disease; and diseases of unknown causes such as sarcoidosis, Crohn's disease and cat-scratch fever.

Examples of TNFα related disorders include, but are not limited to, those described in WO 98/03502 and WO 98/54170, both of which are incorporated herein in their entireties by reference. Specific examples include, but are not limited to: endotoxemia or toxic shock syndrome; cachexia; adult respiratory distress syndrome; bone resorption diseases such as arthritis; hypercalcemia; Graft versus Host Reaction; cerebral malaria; inflammation; tumor growth; chronic pulmonary inflammatory diseases; reperfusion injury; myocardial infarction; stroke; circulatory shock; rheumatoid arthritis; Crohn's disease; HIV infection and AIDS; other disorders such as rheumatoid arthritis, rheumatoid spondylitis, osteoarthritis, psoriatic arthritis and other arthritic conditions, septic shock, septis, endotoxic shock, graft versus host disease, wasting, Crohn's disease, ulcerative colitis, multiple sclerosis, systemic lupus erythromatosis, ENL in leprosy, HIV, AIDS, and opportunistic infections in AIDS; disorders such as septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, oncogenic or cancerous conditions, asthma, autoimmune disease, radiation damages, and hyperoxic alveolar injury; viral infections, such as those caused by the herpes viruses; viral conjunctivitis; or atopic dermatitis.

In other embodiments, the use of formulations, compositions or dosage forms provided herein in various immunological applications, in particular, as vaccine adjuvants, particularly anticancer vaccine adjuvants, as disclosed in U.S. Publication No. 2007/0048327, published Mar. 1, 2007, which is incorporated herein in its entirety by reference, is also encompassed. These embodiments also relate to the uses of the compositions, formulations, or dosage forms provided herein in combination with vaccines to treat or prevent cancer or infectious diseases, and other various uses such as reduction or desensitization of allergic reactions.

5. EXAMPLES

Embodiments provided herein may be more fully understood by reference to the following examples. These examples are meant to be illustrative of pharmaceutical compositions and dosage forms provided herein, but are not in any way limiting.

5.1. Core Formulation

Table 1 illustrates a batch formulation and oral dosage formulation for a core portion containing Compound A.

TABLE 1

| Trade Name | Common Name | Weight Percent |
|---|---|---|
| Compound A | | 10.00% |
| 316, Fast-Flo ® | Lactose Monohydrate | 60.00% |
| Avicel ®PH-102 | Microcrystalline Cellulose | 26.25% |
| Ac-Di-Sol ® | Croscarmellose Sodium | 3.00% |
| | Magnesium stearate | 0.75% |
| | | 100.0% |

The core formulation was prepared according to the weight percentage provided above. In the table, the value of Compound A assumes the potency of 100% w/w. The actual input weight was adjusted depending on the assigned purity and water content. Lactose was adjusted to maintain the batch weight.

5.2. Coating Formulations

5.2.1. Coating Formulation 1

Three coating formulations, having pink, brown and beige color, respectively, were made using the ingredients listed in Table 2 below:

TABLE 2

| Ingredient (% w/w) | Pink | Brown | Beige |
|---|---|---|---|
| Poly Vinyl Alcohol | 40.0 | 40.0 | 40.0 |
| Macrogol/PEG 3350 | 20.2 | 20.2 | 20.2 |
| Talc | 14.8 | 14.8 | 14.8 |
| Titanium Dioxide | 24.6 | 12.13 | 22.99 |
| Red Iron Oxide | 0.4 | 1.22 | 1.18 |
| Yellow Iron Oxide | — | 11.65 | 0.43 |
| Black Iron Oxide | — | — | 0.4 |

5.2.2. Coating Formulation 2

Three coating formulations, having pink, brown and beige color, respectively, were made using the ingredients listed in Table 3 below:

TABLE 3

| Ingredient (% w/w) | Pink | Brown | Beige |
|---|---|---|---|
| Lactose Monohydrate | 33.0 | 33.0 | 31.0 [correct?] |
| Hypromellose 6 cP | 31.0 | 31.0 | 31.0 |
| Macrogol/PEG 3350 | 5.0 | 5.0 | 5.0 |
| Triacetin | 4.0 | 4.0 | 4.0 |
| Titanium Dioxide | 26.5 | 12.47 | 26.0 [correct?] |
| Red Iron Oxide | 0.5 | 2.1 | 1.7 |
| Yellow Iron Oxide | — | 12.43 | 0.6 |
| Black Iron Oxide | — | — | 0.7 |

5.2.3. Coating Formulation 3

Three coating formulations, having pink, brown and beige color, respectively, were made using the ingredients listed in Table 4 below:

TABLE 4

| Ingredient (% w/w) | Pink | Brown | Beige |
|---|---|---|---|
| Polydextrose FCC | 26.0 | 26.0 | 26.0 |
| Hypromellose 15 cP | 31.0 | 31.0 | 31.0 |
| Talc | 7.0 | 7.0 | 7.0 |
| Maltodextrin | 5.0 | 5.0 | 5.0 |
| Medium Chain Triglycerides | 2.0 | 2.0 | 2.0 |
| Titanium Dioxide | 28.5 | 14.47 | 26.0 |
| Red Iron Oxide | 0.5 | 2.1 | 1.7 |
| Yellow Iron Oxide | — | 12.43 | 0.6 |
| Black Iron Oxide | — | — | 0.7 |

5.2.4. Coating Formulation 4

Three coating formulations, having pink, brown and beige color, respectively, were made using the ingredients listed in Table 5 below:

TABLE 5

| Ingredient (% w/w) | Pink | Brown | Beige |
|---|---|---|---|
| Polydextrose FCC | 26.0 | 26.0 | 26.0 |
| Hypromellose 15 cP | 31.0 | 31.0 | 31.0 |
| Talc | 7.0 | 7.0 | 7.0 |
| Maltodextrin | 5.0 | 5.0 | 5.0 |
| Titanium Dioxide | 30.5 | 16.47 | 28.0 |
| Red Iron Oxide | 0.5 | 2.1 | 1.7 |
| Yellow Iron Oxide | — | 12.43 | 0.6 |
| Black Iron Oxide | — | — | 0.7 |

5.2.5. Coating Formulation 5

Three coating formulations, having pink, brown and beige color, respectively, were made using the ingredients listed in Table 6 below:

TABLE 6

| Ingredient (% w/w) | Pink | Brown | Beige |
|---|---|---|---|
| Polydextrose FCC | 26.0 | 26.0 | 26.0 |
| Hypromellose 15 cP | 31.0 | 31.0 | 31.0 |
| Talc | 7.0 | 7.0 | 7.0 |
| Maltodextrin | 5.0 | 5.0 | 5.0 |
| Triacetin | 4.0 | 4.0 | 4.0 |
| Titanium Dioxide | 26.5 | 12.47 | 24.0 |
| Red Iron Oxide | 0.5 | 2.1 | 1.7 |
| Yellow Iron Oxide | — | 12.43 | 0.6 |
| Black Iron Oxide | — | — | 0.7 |

5.2.6. Coating Formulation 6

Three coating formulations, having pink, brown and beige color, respectively, were made using the ingredients listed in Table 7 below:

TABLE 7

| Ingredient (% w/w) | Pink | Brown | Beige |
|---|---|---|---|
| Polydextrose FCC | 13.0 | 13.0 | 13.0 |
| Hypromellose 15 cP | 44.0 | 44.0 | 44.0 |
| Talc | 7.0 | 7.0 | 7.0 |
| Maltodextrin | 5.0 | 5.0 | 5.0 |
| Medium Chain Triglycerides | 4.0 | 4.0 | 4.0 |
| Titanium Dioxide | 26.5 | 12.47 | 24.0 |
| Red Iron Oxide | 0.5 | 2.1 | 1.7 |
| Yellow Iron Oxide | — | 12.43 | 0.6 |
| Black Iron Oxide | — | — | 0.7 |

5.3. Tablet Formulation (Core+Coating)

A complete tablet formulation, including core and coating, was prepared using the ingredients listed in Table 8 below:

| Ingredient (% w/w) | Pink | Brown | Beige |
|---|---|---|---|
| Core | | | |
| Compound A | 10.00 | 10.00 | 10.00 |
| Lactose Monohydrate (316, Fast-Flo ®) | 60.00 | 60.00 | 60.00 |
| Microcrystalline Cellulose (Avicel ® PH-102) | 26.25 | 26.25 | 26.25 |
| Croscarmellose Sodium (Ac-di-sol ®) | 3.00 | 3.00 | 3.00 |
| Magnesium Stearate | 0.75 | 0.75 | 0.75 |
| Total | 100 | 100 | 100 |
| Coating | | | |
| Poly Vinyl Alcohol | 40.00 | 40.00 | 40.00 |
| Macrogol/PEG 3350 | 20.20 | 20.20 | 20.20 |
| Talc | 14.80 | 14.80 | 14.80 |
| Titanium Dioxide | 24.60 | 12.13 | 22.99 |
| Red Iron Oxide | 0.40 | 1.22 | 1.18 |
| Yellow Iron Oxide | — | 11.65 | 0.43 |
| Black Iron Oxide | — | — | 0.40 |
| Total | 100 | 100 | 100 |

5.4. Stability of Formulation

Tablets were coated with different color formulations based on the poly vinyl alcohol. (See Section 5.3, above). Color coating was applied to achieve 4% weight gain of core formulations. For some of the tablets, coating was continued with clear coating suspension to achieve a target of 1% weight gain (i.e., a total of 5% weight gain). Tablets were placed in open dish stability chambers under accelerated temperature and humidity conditions (40° C./75% RH) to assess color changes.

There was no color fading observed for tablets after 24 hours, 48 hours and 72 hours. A slight dullness in the color was observed for color and clear coated tablets after 72 hours. The results indicate that the formulation described in Section 5.3 above, with or without clear coating, have adequate stability, particularly with regard to color changes.

While examples of certain particular embodiments are provided herein, it will be apparent to those skilled in the art that various changes and modifications may be made. Such modifications are also intended to fall within the scope of the appended claims.

What is claimed is:

1. A pharmaceutical composition in the form of an oral tablet comprising:

a) a core composition, wherein the core composition comprises compound A:

(A)

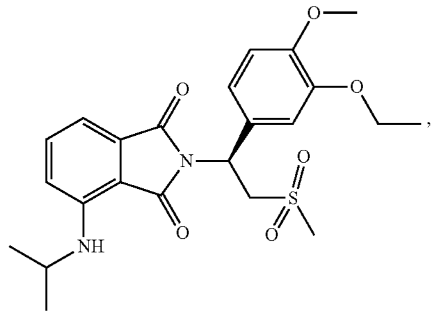

or a pharmaceutically acceptable salt thereof, a filler, a disintegrant, and a lubricant, wherein the filler comprises i) lactose monohydrate in an amount of 50% to 65% by weight of the pharmaceutical composition and ii) cellulose in an amount of 15% to 40% by weight of the pharmaceutical composition, and b) a coating formulation comprising polyvinyl alcohol, wherein the coating formulation does not contain medium chain triglycerides (MCTs) and no color fading of the tablet is observed at 48 hours when placed in an open dish stability chamber maintained at 40° C. and 75% relative humidity.

2. The pharmaceutical composition of claim 1, wherein compound A is present in an amount of 5% to 25% by weight of the pharmaceutical composition.

3. The pharmaceutical composition of claim 1, wherein the disintegrant is croscarmellose.

4. The pharmaceutical composition of claim 3, wherein the croscarmellose is present at an amount of 2% to 8% by weight of the pharmaceutical composition.

5. The pharmaceutical composition of claim 3, wherein lactose monohydrate is present at an amount of 60% by weight of the core composition and the croscarmellose is present at an amount of 2% to 8% by weight of the core composition.

6. The pharmaceutical composition of claim 1, wherein the lubricant is magnesium stearate.

7. The pharmaceutical composition of claim 6, wherein the magnesium stearate is present at an amount of 0.25% to 5% of the pharmaceutical composition.

8. The pharmaceutical composition of claim 1, wherein the polyvinyl alcohol is present in an amount of 35% to 45% by weight of the coating formulation.

9. The pharmaceutical composition of claim 1, wherein the coating formulation comprises one or more further excipients, wherein the excipient is a coating agent, a binder, a lubricant, a stabilizing agent, a plasticizer, an adhesive, a glidant, a diluent, or a combination thereof.

10. The pharmaceutical composition of claim 9, wherein the excipient is polyethylene glycol.

11. The pharmaceutical composition of claim 10, wherein the polyethylene glycol is present in an amount of 20% to 25% by weight of the coating formulation.

12. The pharmaceutical composition of claim 9, wherein the excipient is talc.

13. The pharmaceutical composition of claim 12, wherein the talc is present in an amount of 10% to 15% by weight of the coating formulation.

14. The pharmaceutical composition of claim 9, further comprising one or more coloring agents.

15. The pharmaceutical composition of claim 14, wherein the coloring agents are present in an amount of 25% to 30% by weight of the coating formulation.

16. The pharmaceutical composition of claim 1, wherein the core composition comprises:

(i) compound A or a pharmaceutically acceptable salt thereof, in an amount of 10% by weight of the core composition;

(ii) lactose monohydrate in an amount of 60% by weight of the core composition;

(iii) microcrystalline cellulose in an amount of 26.25% by weight of the core composition;

(iv) croscarmellose in an amount of 3% by weight of the core composition; and (v) magnesium stearate in an amount of 0.75% by weight of the core composition.

17. The pharmaceutical composition of claim 16, wherein the coating formulation comprises:

(i) polyvinyl alcohol in an amount of 40% by weight of the coating formulation;

(ii) polyethylene glycol in an amount of 20% by weight of the coating formulation;

(iii) talc in an amount of 15% by weight of the coating formulation; and (iv) a mixture of coloring agents in an amount of 25% by weight of the coating formulation.

18. A method of treating a disease or disorder in a patient, the method comprising administering to the patient the pharmaceutical composition of claim 1, wherein the disease or disorder is selected from the group consisting of psoriasis, arthritis, dermatitis, acne, dermatomyositis, and ulcerative colitis, Behcet's disease, Crohn's disease, sarcoidosis, uveitis, rosacea and lichen planus.

19. The method of claim 18, wherein the psoriasis is plaque-type psoriasis.

20. The method of claim 18, wherein the arthritis is psoriatic arthritis.

21. The method of claim 18, wherein the disease is Behcet's disease.

* * * * *